United States Patent
Bothe et al.

(10) Patent No.: US 9,512,169 B2
(45) Date of Patent: Dec. 6, 2016

(54) 3-SUBSTITUTED ESTRA-1,3,5(10),16-TETRAENE DERIVATIVES, METHODS FOR THE PRODUCTION THEREOF, PHARMACEUTICAL PREPARATIONS CONTAINING SAME, AND USE THEREOF FOR THE PRODUCTION OF MEDICAMENTS

(71) Applicant: BAYER PHARMA AKTIENGESELLSCHAFT, Berlin (DE)

(72) Inventors: Ulrich Bothe, Berlin (DE); Matthias Busemann, Berlin (DE); Oliver Martin Fischer, Berlin (DE); Naomi Barak, Berlin (DE); Andrea Rotgeri, Berlin (DE); Tobias Marquardt, Wuppertal (DE); Christian Stegmann, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 23 days.

(21) Appl. No.: 14/414,386

(22) PCT Filed: Jul. 5, 2013

(86) PCT No.: PCT/EP2013/064257
§ 371 (c)(1),
(2) Date: Jan. 12, 2015

(87) PCT Pub. No.: WO2014/009274
PCT Pub. Date: Jan. 16, 2014

(65) Prior Publication Data
US 2015/0210734 A1    Jul. 30, 2015

(30) Foreign Application Priority Data
Jul. 10, 2012 (DE) .................. 10 2012 211 970

(51) Int. Cl.
*A61K 31/58* (2006.01)
*C07J 43/00* (2006.01)

(52) U.S. Cl.
CPC .............. *C07J 43/003* (2013.01); *A61K 31/58* (2013.01)

(58) Field of Classification Search
CPC ............................ C07J 43/003; A61K 31/58
USPC ........................................... 540/95; 514/176
See application file for complete search history.

(56) References Cited

U.S. PATENT DOCUMENTS

| | | |
|---|---|---|
| 5,604,213 A | 2/1997 | Barrie et al. |
| 6,541,463 B1 | 4/2003 | Labrie et al. |
| 2005/0203075 A1 | 9/2005 | Agoston et al. |
| 2010/0190826 A1 | 7/2010 | Kakefuda et al. |

FOREIGN PATENT DOCUMENTS

| | | |
|---|---|---|
| WO | WO-9831702 | 7/1998 |
| WO | WO-9845315 | 10/1998 |
| WO | WO-9946279 | 9/1999 |
| WO | WO-0007576 | 2/2000 |
| WO | WO-2007100066 | 9/2007 |
| WO | WO-2008065100 | 6/2008 |
| WO | WO-2008077810 | 7/2008 |
| WO | WO-2013045407 | 4/2013 |

OTHER PUBLICATIONS

Azzarello, Joseph T, "Expression of AKR1C3 in Renal Cell Carcinoma, Papillary Urothelial Carcinoma, and Wilms' Tumor", Int J Clin Exp Pathol, 3(2), (2009), 147-155.
Birtwistle, Jane, "The Aldo-Keto Reductase AKR1C3 Contributes to 7,12-Dimethylbenz(A) Anthracene-3,4-Dihydrodiol Mediated Oxidative DNA Damage in Myeloid Cells: Implications for Leukemogenesis", Mutat Res, 662(1-2), (2009), 67-74.
Bydal, Patrick, "Steroidal Lactones As Inhibitors of 17β-hydroxysteroid Dehydrogenase Type 5: Chemical Synthesis, Enzyme Inhibitory Activity, and Assessment of Estrogenic and androgenic activities", Eur J of Med Chem, 44, (2009), 632-644.
Byrns, "Aldo-keto Reductase 1C3 Expression in MCF-7 Cells Reveals Roles in Steroid Hormone and Prostglandin Metabolism That May Explain Its Over-Expression in Breast Cancer", J Steroid Biochem Mol Biol, 118(3), (2010), 177-187.
Byrns, Michael C, "Inhibitors of Type 5 17β-hydroxysteroid Dehydrogenase (AKR1C3): Overview and Structural Insights", Journal Steroid Biochem Molecular Biology, 125, (2011), 95-104.
Cacchi, Sandro, "Palladium-Catalyzed Reaction of Enol Triflates with 1-Alkynes. A New Route to Conjugated Enynes", Synthesis, 4, (1986), 320-322.
Colombe, Laurent, "Prostaglandin Metabolism in Human Hair Follicle", Exp Dermatol, 16(9), (2007), 762-769.
Czako, Barbara, "Discovery of Potent and Practical Antiangiogenic Agents Inspired by Cortistatin A", JACS, 131, (2009), 9014-9019.
Day, Joanna M, "Design and Validation of Specific Inhibitors of 17β-hydroxysteroid Dehydrogenases for Therapeutic Application in Breast and Prostate Cancer, and in Endometriosis", Endocrine-Related Cancer, 15, (2008), 665-692.

(Continued)

*Primary Examiner* — Barbara P Badio
(74) *Attorney, Agent, or Firm* — Resek Liang & Frank LLP; Stanley D. Liang

(57) ABSTRACT

The invention relates to AKR1C3 inhibitors and to processes for their preparation, to their use for the treatment and/or prophylaxis of diseases and also to their use for preparing medicaments for the treatment and/or prophylaxis of diseases, in particular bleeding disorders and endometriosis.

10 Claims, No Drawings

(56) References Cited

OTHER PUBLICATIONS

Deluca, Dominga, "Inhibitory Effects of Fluorine-Substituted Estrogens on the Activity of 17beta-hydroxysteroid Dehydrogenases", Mol. Cell Endocrinol, 248, (2006), 218-224.

Delvoux, Bert, "Increased Production of 17β-Estradiol in Endometriosis Lesions is the Result of Impaired Metabolism", Endocrinol Metab., 94, (2009), 876-883.

Dufort, Isabelle, "Characteristics of a Highly Labile Human Type 5 17β-Hydroxysteroid Dehydrogenase", Endocrinology, 140 , (1999), 568-574.

Figueroa, Jonine D, "Bladder Cancer Risk and Genetic Variation in AKR1C3 and Other Metabolizing Genes", Carcinogenesis, 29(10), (2008), 1955-1962.

Fung, K-M, "Increased Expression of Type 2 3α-hydroxysteroid Dehydrogenase/type 5 17β-Hydroxysteroid Dehydrogenase (AKR1C3) and Its Relationship with Androgen Receptor in Prostate Carcinoma ", Endocr Relat Cancer, 13(1), (2006), 169-180.

Haider, Samer, "Novel Steroidal Pyrimidyl Infibitors of P450 17 (17α-hydroxylase/C17-20 lyase)", Archiv der Pharmizie,(Weinheim, Germany) 334, 12, (2001), 373-374.

Halim, Marlin, "Imaging Induction of Cytoprotective Enzymes in Intact Human Cells: Coumberone, a Metabolic Reporter for Human AKR1C Enzymes Reveals Activation by Panaxytriol, an Active Component of Red Ginseng", J. Am. Chem. Soc., 130, (2008), 14123-14128.

Harnisch, Wolfram, "A Novel Approach to Cardenolides", J. Org. Chem., 50, (1985), 1990-1992.

He, Chunyan, "A Large-Scale Candidate Gene Association Study of Age at Menarche and Age at Natural Menopause", Hum Genet, 125(5), (2010), 515-527.

Heck, R. F., "Palladium-Catalyzed Vinylic Hydrogen Substitution Reactions with Aryl, Benzyl, and Styryl Halides", J. Org. Chem., vol. 37, N. 14, (1972), 2320-2322.

Horwitz, Jerome, "In Vitro Inhibition of Estrogen Sulfoconjugation by Some 2- and 4-Substituted Estra-1,3,5(10)-trien-17β-ols", J. Med Chem, 29, (1986), 692-698.

Knapp, David M, "A General Solution for Unstable Boronic Acids:Slow-Release Cross-Coupling from Air-Stable MIDA Boronates", J. Am. Chem. Soc., 131, (2009), 6961-6963.

Lan, Qing, "Genetic Polymorphisms in the Oxidative Stress Pathway and Susceptibility to Non-Hodgkin Lymphoma", Hum Genet, 121(2), (2007), 161-168.

Lan, Qing, "Oxidative Damage-Related Genes AKR1C3 and 0GG1 Modulate Risks for Lung Cancer Due to Exposure to PAH-Rich Coal Combustion Emissions", Carcinogenesis, 25(11), (2004), 2177-2181.

Li, Rui, "Abiraterone Inhibits 3β-Hydroxysteroid Dehydrogenase: A Rationale for Increasing Drug Exposure in Castration-Resistant Prostate Cancer", Clin Cancer Res, 18 (13), (2012), 3571-3579.

Lovering, Andrew L, "Crystal Structures of Prostaglandin D2 11-Ketoreductase (AKR1C3) in Complex with the Nonsteroidal Anti-Inflammatory Drugs Flufenamic Acid and Indomethacin", Cancer Res, 64(5), (2004), 1802-1810.

Molander, Gary A, "Scope of the Suzuki—Miyaura Cross-Coupling Reactions of Potassium Heteroaryltrifluoroborates", J. Org. Chem., 74, (2009), 973-980.

Moreira, V. M., "CYP17 Inhibitors for Preostate Cancer Treatment—An Update", Curr Med Chem., vol. 15, No. 9, (2008), 868-899.

Mostaghel, Elahe A, "Resistance to CYP17A1 Inhibition with Abiraterone in Castraion-Resistant Prostate Cancer: Induction of Steroidogenesis and Androgen Receptor Splice Variants", Clin Cancer Res, 17 (18), (2011), 5913-5925.

Oster, Alexander, "Bicyclic Substituted Hydroxyphenylmethanones as Novel Inhibitors of 17β-Hydroxysteroid Dehydrogenase Type 1 (17β-HSD1) for the Treatment of Estrogen-Dependent Diseases", J. Med. Chem., (2010), 8176-8186.

Penning, Trevor M, "Aldo-keto Reductase (AKR) 1C3: Role in Prostate Disease and the Development of Specific Inhibitors", Mol Cell Endocrinol, 248 (1-2), (2006), 182-191.

Pierrou, Stefan, "Expression of Genes Involved in Oxidative Stress Responses in Airway Epithelial Cells of Smokers with Chronic Obstructive Pulmonary Disease", Am J Respir Crit Care, 175(6), (2007), 577-586.

Potter, "Novel Steroidal Inhibitors of Human Cytochrome P45017α (17α-Hydroxylase-C17,20-lyase); Potential Agents for the Treatment of Prostatic Cancer", J. Med. Chem., 38, (1995), 2463-2471.

Qin Kenan, "Identification of a Functional Polymorphism of the Human Type 5 17β-Hydroxysteroid Dehydrogenase Gene Associated with Polycystic Ovary Syndrome", J. Endocrinol Metab, 91(1), (Jan. 1, 2006), 270-276.

Rizner, Tea Lanisnik, "AKR1C1 and AKR1C3 May Determine Progesterone and Estrogen Ratios in Endometrial Cancer", Mol Cell Endocrinol, 248(1-2), (2006), 126-135.

Roberts, "Polymorphisms in Genes Involved in Sex Hormone Metabolism May Increase Risk of Benign Prostatic Hyperplasia", Prostate, 66(4), (2006), 392-404.

Smuc, Tina, "Disturbed Estrogen and Progesterone Action in Ovarian Endometriosis", Mol Cell Endocrinol, 301 (1-2), (Mar. 25, 2009), 59-64.

Svensson, Per-Arne, "Regulation of Human Aldoketoreductase 1C3 (AKR1C3) Gene Expression in the Adipose Tissue", Cell Mol Biol Lett, 13(4), (2008), 599-613.

Yee, Dominic J, "Flurogenic Metabolic Probes for Direct Activity Readout of Redox Enzymes: Selective Measurement of Human AKR1C2 in Living Cells", Proc. Natl. Acad. Sci., 103, (2006), 13304-13309.

Zhang Xuqing, "An efficient synthesis of novel estrieno[2.3-b] and [3.4-c]pyrroles", Tetrahedron Letters, 43, (Jan. 1, 2003), 3071-3074.

3-SUBSTITUTED ESTRA-1,3,5(10),16-TETRAENE DERIVATIVES, METHODS FOR THE PRODUCTION THEREOF, PHARMACEUTICAL PREPARATIONS CONTAINING SAME, AND USE THEREOF FOR THE PRODUCTION OF MEDICAMENTS

The invention relates to AKR1C3 inhibitors and to processes for their preparation, to their use for the treatment and/or prophylaxis of diseases and also to their use for preparing medicaments for the treatment and/or prophylaxis of diseases, in particular bleeding disorders and endometriosis.

AKR1C3 is a multifunctional enzyme and catalyses inter alia the reduction of 4-androstene-3,17-dione (a weak androgen) to testosterone (a potent androgen) and of oestrone (a weak oestrogen) to 17β-oestradiol (a strong oestrogen). In addition, the reduction of prostaglandin (PG) H2 to PGF2α and PGD2 to 9α, 11β-PGF2 is inhibited (T. M. Penning et. al., 2006, 'Aldo-keto reductase (AKR) 1C3: Role in prostate disease and the development of specific inhibitors', Molecular and Cellular Endocrinology 248(1-2), 182-191).

The local formation of oestradiol (E2) plays a central role in the initiation and progression of breast cancer disorders and endometriosis. Reduction of the tissue concentrations of oestrogens and in particular of oestradiol is achieved by therapeutic administration of aromatase inhibitors (to inhibit the formation of oestrogens from androgens) and of sulphatase inhibitors (to block the formation of oestrone from oestrone sulphate). However, both therapeutic approaches have the disadvantage that systemic oestrogen concentrations are radically reduced (A. Oster et. al., *J. Med. Chem.* 2010, 53, 8176-8186). Recently, it has been demonstrated experimentally that endometriotic lesions are capable of synthesizing oestradiol locally (B. Delvoux et al., J Clin Endocrinol Metab. 2009, 94, 876-883). For the subtype of ovarial endometriosis, an overexpression of AKR1C3 mRNA has been described (T. Smuc et al., Mol Cell Endocrinol. 2009 Mar. 25; 301(1-2): 59-64).

There is a great need to identify novel inhibitors of the enzyme aldo-keto reductase 1C3 (AKR1C3) (synonyms: type 5 17β-hydroxysteroid dehydrogenase or prostaglandin F synthase), since inhibitors have potential for the treatment of hormone-dependent disorders such as, for example, endometriosis, but also for the treatment of hormone-independent disorders (M. C. Byrns, Y. Jin, T. M. Penning, Journal of Steroid Biochemistry and Molecular Biology (2010); A. L. Lovering et. al., *Cancer Res* 64(5), 1802-1810). In addition to endometriosis, this also includes prostate cancer (K. M. Fung et al., *Endocr Relat Cancer* 13(1), 169-180), prostate hyperplasia (R. O. Roberts et al., *Prostate* 66(4), 392-404), endometrial carcinoma (T. L. Rizner et al., *Mol Cell Endocrinol* 2006 248(1-2), 126-135), polycystic ovary syndrome (K. Qin et al., *J Endocrinol Metab* 2006, 91(1), 270-276), lung carcinoma (Q. Lan et al., *Carcinogenesis* 2004, 25(11), 2177-2181), non-Hodgkin lymphoma (Q. Lan et al., *Hum Genet* 2007, 121(2), 161-168), hair loss (L. Colombe et al., *Exp Dermatol* 2007, 16(9), 762-769), adiposity (P. A. Svensson et al., *Cell Mol Biol Lett* 2008, 13(4), 599-613), bladder carcinoma (J. D. Figueroa, *Carcinogenesis* 2008, 29(10), 1955-1962), chronic myeloid leukaemia (J. Birthwistle, *Mutat Res* 2009, 662(1-2), 67-74), renal cell carcinoma (J. T. Azzarello, *Int J Clin Exp Pathol* 2009, 3(2), 147-155), breast cancer (M. C. Byrns, *J Steroid Biochem Mol Biol* 2010, 118(3), 177-187), premature sexual maturity (C. He, *Hum Genet* 2010, 128(5), 515-527) and chronic obstructive pulmonary disease (S. Pierrou, *Am J Respir Crit Care* 2007, 175(6), 577-586).

Some inhibitors of AKR1C3 are known (review: Joanna M Day, Helena J Tutill, Atul Purohit and Michael J Reed, Endocrine-Related Cancer (2008) 15, 665-692 see also patents US20100190826 and WO2007/100066). A steroidal substance that has been described is, for example, EM-1404, which is based on the oestratriene skeleton having a spirolactone unit in position 17 (F. Labrie et al. U.S. Pat. No. 6,541,463, 2003).

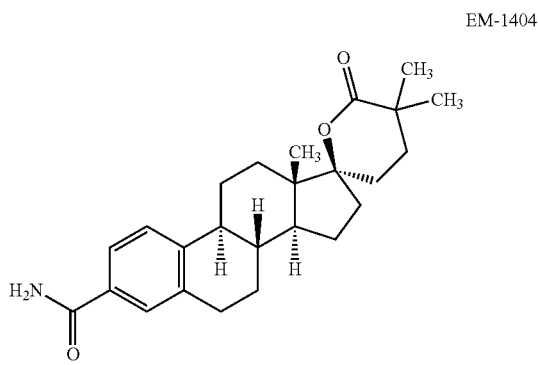

EM-1404

Further steroidal AKR1C3 inhibitors having a lactone unit are found in P. Bydal, Van Luu-The, F. Labrie, D. Poirier, European Journal of Medicinal Chemistry 2009, 44, 632-644. Fluorinated oestratriene derivatives have been described in D. Deluca, G. Moller, A. Rosinus, W. Elger, A. Hillisch, J. Adamski, Mol. Cell. Endocrinol. 2006, 248, 218-224.

The compounds according to the invention are substances based on an oestra-1,3,5(10),16-tetraene skeleton substituted by an aromatic heterocycle in position 17. S. E. Barrie et al. U.S. Pat. No. 5,604,213 describe 17-(3-pyridyl)estra-1,3,5(10),16-tetraen-3-ol, a related substance substituted at carbon atom 3 by a free hydroxyl group, only as a 17α-hydroxylase/C17-20 lyase (Cyp17A1) inhibitor.

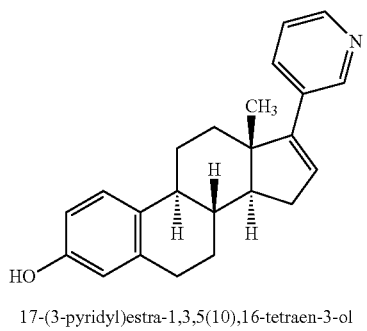

17-(3-pyridyl)estra-1,3,5(10),16-tetraen-3-ol

In addition, U.S. Pat. No. 5,604,213 does not describe any 17-(3-pyridyl)estra-1,3,5(10),16-tetraene derivatives substituted by an alkoxy or an alkyl group in position 3. The substituents at the 3-position of the compounds according to the invention claimed in the present invention additionally comprise one or more functional groups such as, for example, carboxyl groups or hydroxyl groups, resulting in a further structural difference to the substances described in U.S. Pat. No. 5,604,213. Surprisingly, it has now been found that the compounds according to the invention claimed herein are potent inhibitors of AKR1C3.

Estra-1,3,5(10),16-tetraene derivatives substituted by an aminocarbonyl (—CONH$_2$) group in position 3 are described in US 2005/0203075 as antiproliferatively and antiangiogenically active, without reference to a concrete molecular target. However, these derivatives are not substituted by a heterocycle in position 17 of the estra-1,3,5(10),16-tetraene skeleton.

A review of 17-pyridyl- and 17-pyrimidylandrostane derivatives described as Cyp17A1 inhibitors is found in V. M. Moreira et al. *Current Medicinal Chemistry*, 2008 Vol. 15, No. 9.

Compounds according to the invention are the compounds of the formula (I) and their salts, solvates and solvates of the salts, and also the compounds comprised by (I) and mentioned hereinbelow as embodiments and their salts, solvates and solvates of the salts.

The present invention provides compounds of the formula (I)

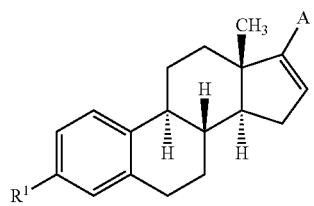

(I)

in which

A represents pyridin-3-yl, pyrimidin-5-yl, pyrimidin-4-yl, pyrazin-2-yl, pyridazin-4-yl, pyridazin-3-yl, optionally mono- or disubstituted by fluorine, chlorine, nitrile, hydroxyl, carboxyl, trifluoromethyl, pentafluoroethyl, methoxy, ethoxy, trifluoromethoxy, —OCH$_2$CF$_3$, —SO$_2$CH$_3$, —SO$_2$CH$_2$CH$_3$, —(C=O)CH$_3$, C$_1$-C$_4$-alkyl, —CH$_2$OH, —C(CH$_3$)$_2$OH, —CONH$_2$, —(C=O)NHCH$_3$, —(C=O)NHCH$_2$CH$_3$, —(C=O)N(CH$_3$)$_2$, —SO$_2$NH$_2$, —SO$_2$NHCH$_3$, —SO$_2$N(CH$_3$)$_2$, R$^1$ represents —O—CR$^a$R$^b$—Y where R$^a$ and R$^b$ independently of one another represent hydrogen, methyl, ethyl, propyl, isopropyl, phenyl, 4-fluorophenyl, 3-fluorophenyl, 2-fluorophenyl, CH$_3$—O—CH$_2$—, —CH$_2$CF$_3$ or R$^a$ and R$^b$ together represent —(CH$_2$)$_n$— where n=2, 3, 4 or 5 or R$^a$ and R$^b$ together represent —CH$_2$—O—CH$_2$—, —CH$_2$—NH—CH$_2$—, —CH$_2$—N(CH$_3$)—CH$_2$—, —CH$_2$CH$_2$—O—CH$_2$CH$_2$—, —CH$_2$CH$_2$—NH—CH$_2$CH$_2$—, —CH$_2$CH$_2$—N(CH$_3$)—CH$_2$CH$_2$—

—O—CR$^c$R$^d$—CR$^e$R$^f$—Y where

R$^c$, R$^d$, R$^e$R$^f$ represent hydrogen or

R$^e$, R$^f$ represent hydrogen and R$^c$, R$^d$ independently of one another represent methyl, ethyl or together represent —(CH$_2$)$_n$— where n=2, 3,4, 5 or together represent —CH$_2$—O—CH$_2$— or —CH$_2$CH$_2$—O—CH$_2$CH$_2$— or R$^c$, R$^d$ represent hydrogen and R$^e$, R$^f$ independently of one another represent methyl, ethyl, CF$_3$CH$_2$— or together represent —(CH$_2$)$_n$— where n=2, 3, 4, 5, —CH$_2$CH$_2$—O—CH$_2$CH$_2$—, —CH$_2$CH$_2$—NH—CH$_2$CH$_2$—, —CH$_2$CH$_2$—N(CH$_3$)—CH$_2$CH$_2$—, —CH$_2$—O—CH$_2$—, —CH$_2$—NH—CH$_2$—, —CH$_2$—N(CH$_3$)—CH$_2$— or R$^d$, R$^e$, R$^f$ represent hydrogen and R$^c$ represents methyl, ethyl, trifluoromethyl or R$^c$, R$^d$, R$^f$ represent hydrogen and R$^e$ represents methyl, ethyl, trifluoromethyl, hydroxyl, methoxy, trifluoromethoxy or R$^d$, R$^f$ represent hydrogen and R$^c$, R$^e$ independently of one another represent methyl, ethyl, trifluoromethyl, —O—CH$_2$CH$_2$CH$_2$—Y,
—O—CH$_2$C(CH$_3$)$_2$CH$_2$—Y,
—O—CH$_2$CH$_2$C(CH$_3$)$_2$—Y,
—O—CH$_2$CH$_2$CH(CH$_3$)—Y,
—O—CH$_2$—CH(OH)—CH$_2$—Y
—OCH$_2$CH$_2$CH$_2$CH—Y,
—CH$_2$—Y,
—CR$^g$R$^h$—CR$^i$R$^j$—Y where R$^g$, R$^h$, R$^i$, R$^j$ represent hydrogen or R$^g$, R$^h$, R$^i$ represent hydrogen and R represents methyl, ethyl, trifluoromethyl or R$^i$, R$^j$ represent hydrogen and R$^g$, R$^h$ represent methyl or together represent —CH$_2$—, —CH$_2$CH$_2$—, —CH$_2$CH$_2$CH$_2$— or R$^g$ represents methyl and R$^h$, R$^i$, R$^j$ represent hydrogen, —CH$_2$CH$_2$CH$_2$—Y,
—CH$_2$CH$_2$C(CH$_3$)$_2$—Y or
—CH$_2$CH$_2$CH$_2$CH$_2$—Y and Y —CO$_2$H, —OH, —(C=O)NH$_2$, —(C=O)NHC$_{1-4}$-alkyl, —S(=O)CH$_3$ and their salts, solvates and solvates of the salts.

Preference is given to compounds of the formula (I) in which

A represents pyridin-3-yl, pyrimidin-5-yl, pyrimidin-4-yl, pyrazin-2-yl, pyridazin-4-yl, pyridazin-3-yl, optionally monosubstituted by fluorine, chlorine, nitrile, hydroxyl, carboxyl, trifluoromethyl, methoxy, ethoxy, trifluoromethoxy, —SO$_2$CH$_3$, —(C=O)CH$_3$, C$_1$-C$_4$-alkyl, represents —O—CR$^a$R$^b$—Y where R$^1$ represents —O—CR$^a$R$^b$—Y where R$^a$ and R$^b$ independently of one another represent hydrogen, methyl, ethyl, propyl, isopropyl, phenyl, CH$_3$—O—CH$_2$—, CF$_3$CH$_2$—, —O—CR$^c$R$^d$—CR$^e$R$^f$—Y where R$^c$, R$^d$, R$^e$R$^f$ represent hydrogen or R$^c$, R$^d$ represent hydrogen and R$^e$, R$^f$ independently of one another represent methyl, ethyl, CF$_3$CH$_2$— or R$^d$, R$^e$, R$^f$ represent hydrogen and R$^c$ represent methyl, ethyl or R$^c$, R$^d$, R$^f$ represent hydrogen and R$^e$ represent methyl, ethyl, —O—CH$_2$CH$_2$CH$_2$—Y,
—O—CH$_2$C(CH$_3$)$_2$CH$_2$—Y,
—O—CH$_2$CH$_2$C(CH$_3$)$_2$—Y,
—O—CH$_2$CH$_2$CH(CH$_3$)—Y,
—O—CH$_2$—CH(OH)—CH$_2$—Y or
—CR$^g$R$^h$—CR$^i$R$^j$—Y where R$^g$, R$^h$, R$^i$, R$^j$ represent hydrogen or R$^g$, R$^h$, R$^i$ represent hydrogen and R$^j$ represents methyl, ethyl or R$^i$, R$^j$ represent hydrogen and R$^g$, R$^h$ represent methyl or R$^g$ represents methyl and R$^h$, R$^i$, R$^j$ represent hydrogen and Y represents —CO$_2$H, —OH, —(C=O)NH$_2$, —(C=O)NHC$_{1-4}$-alkyl and their salts, solvates and solvates of the salts.

Particular preference is given to compounds of the formula (I) in which

A represents pyridin-3-yl, pyrimidin-5-yl, pyridazin-4-yl, optionally monosubstituted by fluorine, carboxyl, trifluoromethyl, methyl $R^1$ represents —O—$CR^aR^b$—Y where
  $R^a$ and $R^b$ represent hydrogen or $R^a$ represents hydrogen and $R^b$ represents methyl, ethyl, phenyl or $CH_3$—O—$CH_2$—
  —O—$CR^cR^d$—$CR^eR^f$—Y where
  $R^c$, $R^d$ represent hydrogen and $R^e$, $R^f$ represent methyl
  —O—$CH_2CH_2CH_2$—Y,
  —O—$CH_2C(CH_3)_2CH_2$—Y,
  —O—$CH_2$—CH(OH)—$CH_2$—Y or
  —$CH_2$—$CH_2$—Y and Y represents —$CO_2H$, —OH, —(C=O)$NH_2$, —(C=O)$NHC_{1-4}$-alkyl and their salts, solvates and solvates of the salts.

Very particular preference is given to compounds of the formula (I) in which

A represents 5-fluoropyridin-3-yl, 5-(trifluoromethyl)pyridin-3-yl, 5-carboxypyridin-3-yl, 6-methylpyridin-3-yl, pyrimidin-5-yl, 6-methylpyridazin-4-yl and $R^1$ represents —O—$CR^aR^b$—$CO_2H$,
  —O—$CR^aR^b$—(C=O)$NH_2$,
  —O—$CR^aR^b$—(C=O)$NHCH_2CH_3$ where
  $R^a$ and $R^b$ represent hydrogen or
  $R^a$ represents hydrogen and $R^b$ represents methyl, ethyl, phenyl, $CH_3OCH_2$—,
  —O—$CR^cR^d$—$CR^eR^f$—$CO_2H$ where
  $R^c$, $R^d$ represent hydrogen and $R^e$, $R^f$ represent methyl,
  —O—$CH_2CH_2CH_2$—OH,
  —O—$CH_2CH_2CH_2$—$CO_2H$,
  —O—$CH_2C(CH_3)_2CH_2$—OH or
  —O—$CH_2$—CH(OH)—$CH_2$—OH and their salts, solvates and solvates of the salts.

The invention furthermore provides the compounds
3-[17-(5-fluoropyridin-3-yl)estra-1,3,5(10),16-tetraen-3-yl]propanoic acid
({17-[5-(trifluoromethyl)pyridin-3-yl]estra-1,3,5(10),16-tetraen-3-yl}oxy)acetic acid
{[17-(5-fluoropyridin-3-yl)estra-1,3,5(10),16-tetraen-3-yl]oxy}acetic acid
{[17-(6-methylpyridin-3-yl)estra-1,3,5(10),16-tetraen-3-yl]oxy}acetic acid
{[17-(pyrimidin-5-yl)estra-1,3,5(10),16-tetraen-3-yl]oxy}acetic acid
5-[3-(carboxymethoxy)estra-1,3,5(10),16-tetraen-17-yl]nicotinic acid
{[17-(6-methylpyridazin-4-yl)estra-1,3,5(10),16-tetraen-3-yl]oxy}acetic acid
3-{[17-(5-fluoropyridin-3-yl)estra-1,3,5(10),16-tetraen-3-yl]oxy}-2,2-dimethylpropanoic acid
4-{[17-(5-fluoropyridin-3-yl)estra-1,3,5(10),16-tetraen-3-yl]oxy}butanoic acid
2-{[17-(5-fluoropyridin-3-yl)estra-1,3,5(10),16-tetraen-3-yl]oxy}propanoic acid
2-{[17-(5-fluoropyridin-3-yl)estra-1,3,5(10),16-tetraen-3-yl]oxy}butanoic acid
2-{[17-(5-fluoropyridin-3-yl)estra-1,3,5(10),16-tetraen-3-yl]oxy}-3-methoxypropanoic acid
2-{[17-(3-pyridyl)estra-1,3,5(10),16-tetraen-3-yl]oxy}propanoic acid
2-{[17-(5-fluoropyridin-3-yl)estra-1,3,5(10),16-tetraen-3-yl]oxy}propanamide
3-{[17-(5-fluoropyridin-3-yl)estra-1,3,5(10),16-tetraen-3-yl]oxy}propan-1-ol
3-{[17-(5-fluoropyridin-3-yl)estra-1,3,5(10),16-tetraen-3-yl]oxy}-2,2-dimethylpropan-1-ol
3-{[17-(5-fluoropyridin-3-yl)estra-1,3,5(10),16-tetraen-3-yl]oxy}propan-1,2-diol
{[17-(5-fluoropyridin-3-yl)estra-1,3,5(10),16-tetraen-3-yl]oxy}(phenyl)acetic acid
N-ethyl-2-({17-[5-(trifluoromethyl)pyridin-3-yl]estra-1,3,5(10),16-tetraen-3-yl}oxy)acetamide
and their salts, solvates and solvates of the salts.

It has been found that the estra-1,3,5(10),16-tetraene-3-carbonylamino derivatives provided by the invention act as AKR1C3 inhibitors. The compounds claimed show strong inhibition of AKR1C3 in vitro ($IC_{50}$ values <200 nM) and in most cases even $IC_{50}$ values <50 nM.

Depending on their structure, the compounds according to the invention (cf., for example, Examples 10, 11, 12, 13, 14, 17 and 18) can exist in certain stereoisomeric forms (diastereomers). Accordingly the invention comprises the diastereomers and their respective mixtures. From such mixtures of diastereomers, the stereoisomerically uniform components can be isolated in a known manner.

If the compounds according to the invention can be present in tautomeric forms, the present invention comprises all tautomeric forms.

Preferred salts in the context of the present invention are physiologically acceptable salts of the compounds according to the invention. However, the invention also comprises salts which for their part are not suitable for pharmaceutical applications, but which can be used, for example, for the isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, acetic acid, formic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of customary bases, such as, by way of example and by way of preference, alkali metal salts (for example sodium salts and potassium salts), alkaline earth metal salts (for example calcium salts and magnesium salts) and ammonium salts derived from ammonia or organic amines having 1 to 16 carbon atoms such as, by way of example and by way of preference, ethylamine, diethylamine, triethylamine, ethyldiisopropylamine, monoethanolamine, diethanolamine, triethanolamine, dicyclohexylamine, dimethylaminoethanol, procain, dibenzylamine, N-methylmorpho line, arginine, lysine, ethylenediamine and N-methylpiperidine.

In the context of the invention, solvates are those forms of the compounds according to the invention which, in the solid or liquid state, form a complex by coordination with solvent molecules. Hydrates are a specific form of the solvates where the coordination is with water. In the context of the present invention, preferred solvates are hydrates.

Moreover, the present invention also comprises prodrugs of the compounds according to the invention. The term "prodrugs" includes compounds which for their part may be biologically active or inactive but which, during the time they spend in the body, are converted into compounds according to the invention (for example metabolically or hydrolytically).

In the context of the present invention, unless specified differently, the substituents have the following meanings:

$C_1$-$C_4$-Alkyl represents a straight-chain or branched alkyl radical having 1 to 4 carbon atoms, by way of example and by way of preference methyl, ethyl, propyl, butyl, isopropyl, tert-butyl, isobutyl.

The invention furthermore provides processes for preparing the compounds of the formula (I) according to the invention. The preparation of the compounds (I) according to the invention can be illustrated by the synthesis schemes below:

Some of the compounds according to the invention can be prepared as described in an exemplary manner for the synthesis of Example 1, starting with oestrone (Synthesis scheme 1):

The conversion of oestrone into Intermediate 1 is known from the literature (*Tetrahedron Letters*, 2003, 44, 3071-3074 or *Journal of Medicinal Chemistry*, 1986, 29, 692-698) or can be accomplished by reacting oestrone with 1,1,2,2,3,3,4,4,4-nonafluorobutane-1-sulphonyl fluoride in THF in the presence of potassium carbonate.

Intermediate 2 is prepared by reaction with ethyl acrylate using the Heck reaction (*J. Org. Chem.,* 1972, 37(14), 2320-2322). Preferably, the reaction is carried out using ethyl acrylate, triethylamine, tri-2-tolylphosphine and palladium(II) acetate in acetonitrile.

Intermediate 3 is synthesized by hydrogenation in the presence of palladium on carbon.

The conversion into Intermediate 4 is carried out using trifluoromethanesulphonic anhydride or N,N-bis(trifluoromethanesulphonyl)aniline in the presence of a base such as pyridine, 2,6-dimethylpyridine or 2,6-di-tert-butylpyridine or in the presence of a tertiary amine such as triethylamine or diisopropylethylamine or using alkali metal hexamethylsilazanes or lithium diisopropylamide (LDA) (J. Med. Chem., 1995, 38, 2463-2471, J. Org. Chem., 1985, 50, 1990-1992, J. Am. Chem. Soc., 2009, 131, 9014-9019, Archiv der Pharmazie (Weinheim, Germany), 2001, 334, 12, 373-374). Preferred is the reaction with trifluoromethanesulphonic anhydride in the presence of 2,6-di-tert-butylpyridine in dichloromethane.

Intermediate 5 is prepared via the Suzuki reaction, which is known to the person skilled in the art. To this end, Intermediate 4 is reacted with 5-fluoropyridine-3-boronic acid or with a corresponding boronic ester such as, for example, a pinacol boronate, an MIDA boronate (D. M. Knapp et al. J. Am. Chem. Soc. 2009, 131, 6961) or with a trifluoroborate salt (G. A. Molander et al., J. Org. Chem. 2009, 74, 973). Suitable for use as catalysts are a large number of palladium-containing catalysts such as, for example, tetrakis(triphenylphosphine)palladium(0), bis(triphenylphosphine)palladium(II) dichloride or [1,3-bis(2,6-diisopropylphenyl)imidazol-2-ylidene](3-chloropyridyl)palladium(II) dichloride (CAS 905459-27-0). Alternatively, it is possible to employ a palladium-containing source such as, for example, palladium(II) acetate, palladium(II) chloride or Pd(dba)$_2$ in combination with a phosphorus-containing ligand such as, for example, triphenylphosphine, SPhos (D. M. Knapp et. al., J. Am. Chem. Soc. 2009, 131, 6961) or RuPhos (G. A. Molander, J. Org. Chem. 2009, 74, 973). Preference is given to the reaction with 5-fluoropyridine-3-boronic acid in the presence of bis(triphenylphosphine)palladium(II) chloride.

The preparation of Example 1 starting with Intermediate 5 takes place by hydrolysis of carboxylic esters, which is known to the person skilled in the art. Preference is given to the reaction with aqueous sodium hydroxide solution in THF and ethanol.

Synthesis scheme 1

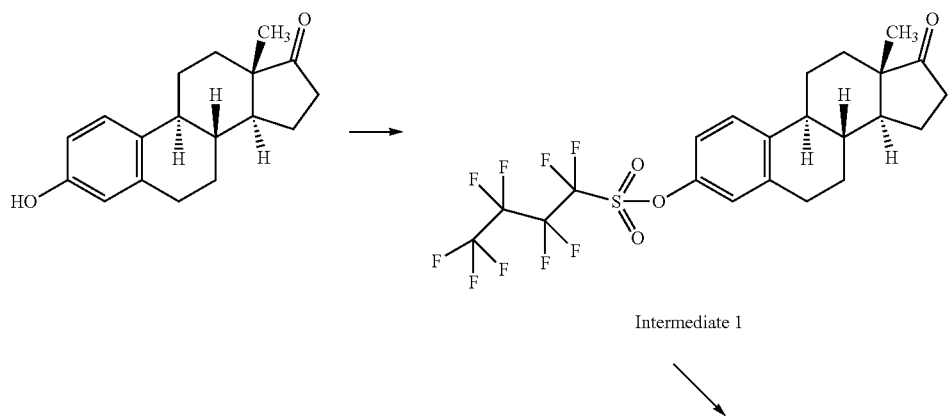

Intermediate 1

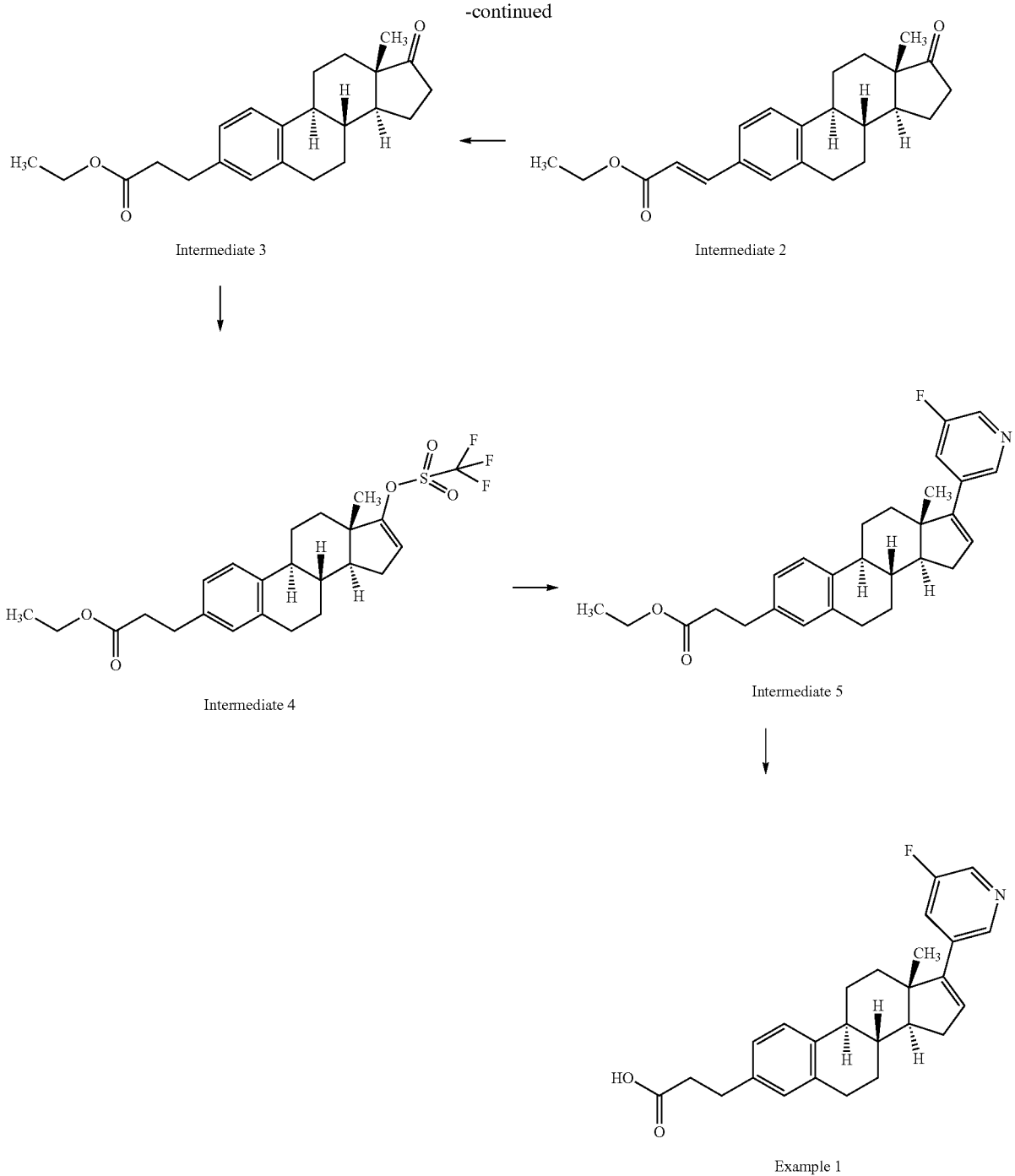

Intermediate 3

Intermediate 2

Intermediate 4

Intermediate 5

Example 1

A further subset of the compounds according to the invention can be prepared as shown in an exemplary manner by the synthesis of Examples 2 to 7 (Synthesis scheme 2):

Starting with oestrone, Intermediate 6 is reacted by reaction with benzyl bromoacetate or benzyl chloroacetate in the presence of a base such as, for example, sodium hydride, potassium tert-butoxide, caesium carbonate or potassium carbonate in DMSO, 1-methylpyrrolidin-2-one, DMF or tetrahydrofuran. Preference is given to the reaction with benzyl bromoacetate in the presence of potassium carbonate in tetrahydrofuran. Intermediate 7 is synthesized analogously to the preparation of Intermediate 4. Starting with Intermediate 7, the Example compounds 2 to 7 are then prepared using reaction conditions as in the preparation of Intermediate 5 by Suzuki reaction. Preference is given to using the appropriate aromatic nitrogenous boronic acids or pinacol boronates. Starting with Example 2,3,4,5,6 and 7, further example compounds can be prepared, as shown in an exemplary manner for the preparation of Example 19. To this end, Example compound 2 (where A is 5-(trifluoromethyl)pyridin-3-yl) is reacted with ethylamine in the course of an amide synthesis reaction, which is known to the person skilled in the art. Preference is given to using 1,1'-carbonyldiimidazole and imidazole hydrochloride in 2-methyltetrahydrofuran, as described in *Organic Process Research & Development* 2009, 13, 106-113.

nitrogenous aromatic boronic acids or pinacol boronates. Preference is given to using 5-fluoropyridine-3-boronic acid (for the preparation of Intermediate 8) or pyridine-3-boronic acid (for the preparation of Intermediate 10). Intermediates 9 and 11 are prepared by reaction with boron tribromide in the presence of 2,6-lutidine in dichloromethane. Preparation of the example compounds takes place by reaction with the

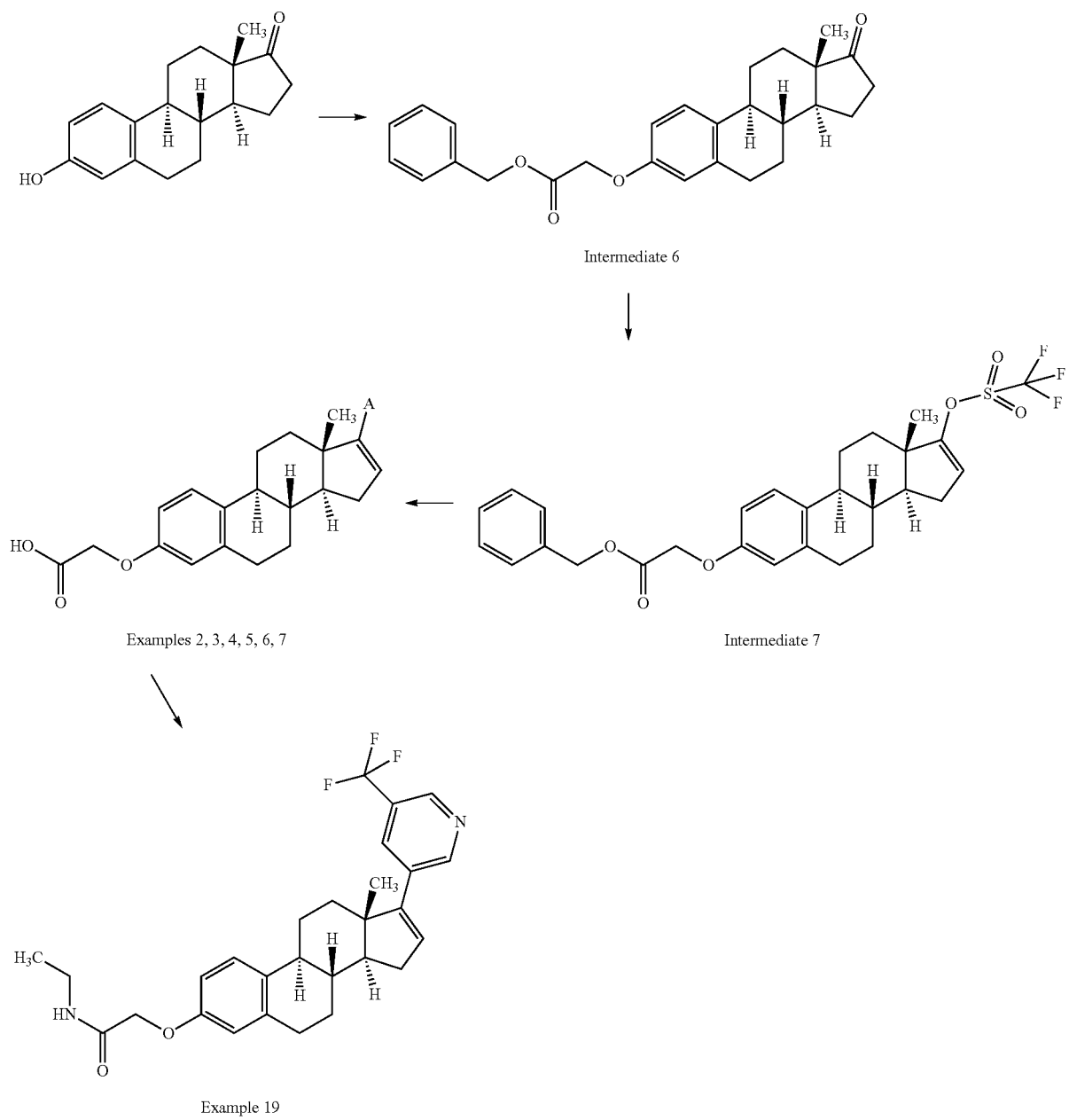

A further subset of the compounds according to the invention can be prepared as shown in an exemplary manner by the synthesis of Examples 8 to 18 (Synthesis scheme 3):

3-Methoxyestra-1,3,5(10),16-tetraen-17-yl trifluoromethanesulphonate (S. Cacchi, E. Morera, *Synthesis*, 1986, 4, 320-322) is prepared analogously to the preparation of Intermediate 5 by Suzuki reaction with the appropriate appropriately substituted alkyl halides in the presence of a base such as sodium hydride, potassium tert-butoxide, caesium carbonate or potassium carbonate. If alkyl chlorides are used, sodium iodide or potassium iodide may optionally be added. Preferred is the reaction with potassium carbonate as base in the presence of potassium iodide or sodium iodide. If the radical R1 of the example compounds contains a carboxyl group, starting with Intermediates 9 and 11 alkyl halides substituted by a methyl carboxylate or ethyl carboxylate group are employed, and in a second step the esters are hydrolyzed by addition of aqueous sodium hydroxide solution.

The present invention furthermore provides medicaments comprising at least one compound according to the invention and at least one or more further active compounds, in particular for the treatment and/or prophylaxis of the disorders mentioned above. The following suitable active com-

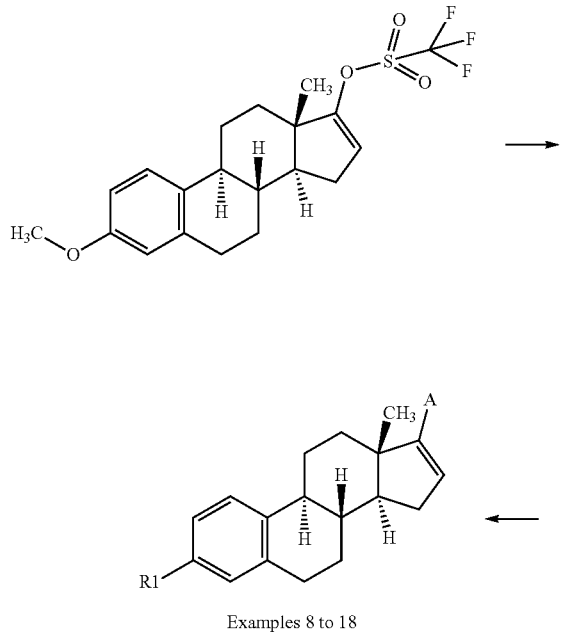

Examples 8 to 18

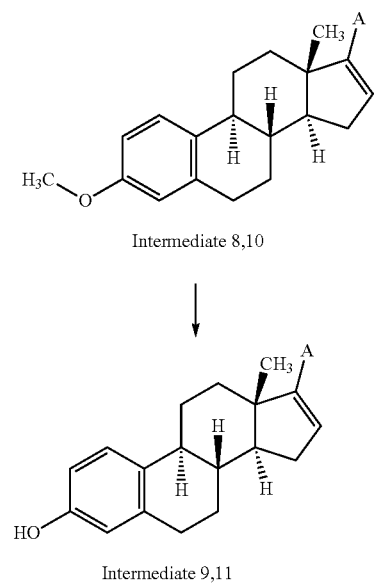

Intermediate 8,10

Intermediate 9,11

In an unforeseeable manner, the compounds according to the invention display a useful spectrum of pharmacological activity and advantageous pharmacokinetic properties. They are therefore suitable for use as medicaments for the treatment and/or prophylaxis of diseases in humans and animals. For the purpose of the present invention, the term "treatment" includes prophylaxis. The pharmaceutical efficacy of the compounds according to the invention can be explained by its action as AKR1C3 inhibitor. Accordingly, the compounds according to the invention are particularly suitable for the treatment and/or prophylaxis of endometriosis, of uterine leiomyomas, of uterine bleeding disorders, of dysmenorrhoea, of prostate carcinoma, of prostate hyperplasia, of acne, of seborrhoea, of hair loss, of premature sexual maturity, of polycystic ovary syndrome, of breast cancer, of lung cancer, of endometrial carcinoma, of renal cell carcinoma, of bladder carcinoma, of non-Hodgkin lymphomas, of chronic obstructive pulmonary disease (COPD), of adiposity or of inflammatory pain.

The present invention furthermore provides the use of the compounds according to the invention for preparing a medicament for the treatment and/or prophylaxis of disorders, in particular the disorders mentioned above.

The present invention furthermore provides a method for the treatment and/or prophylaxis of disorders, in particular the disorders mentioned above, using an effective amount of the compounds according to the invention.

The present invention furthermore provides the use of the compounds according to the invention for the treatment and/or prophylaxis of disorders, in particular the disorders mentioned above.

The present invention furthermore provides the compounds according to the invention for use in a method for the treatment and/or prophylaxis of the disorders mentioned above.

pounds for combinations may be mentioned by way of example and by way of preference: selective oestrogen receptor modulators (SERMs), oestrogen receptor (ER) antagonists, aromatase inhibitors, 17β HSD1 inhibitors, steroid sulphatase (STS) inhibitors, GnRH agonists and antagonists, kisspeptin receptor (KISSR) antagonists, selective androgen receptor modulators (SARMs), androgens, 5α-reductase inhibitors, selective progesterone receptor modulators (SPRMs), gestagens, antigestagens, oral contraceptives, inhibitors of mitogen activating protein (MAP) kinases and inhibitors of the MAP kinases kinases (Mkk3/6, Mek1/2, Erk1/2), inhibitors of the protein kinases B (PKBα/β/γ; Akt1/2/3), inhibitors of the phosphoinositide 3-kinases (PI3K), inhibitors of the cyclin-dependent kinase (CDK1/2), inhibitors of the hypoxia-induced signal path (HIF1alpha inhibitors, activators of prolyl hydroxylases), histone deacetylase (HDAC) inhibitors, prostaglandin F receptor (FP) (PTGFR) antagonists and non-steroidal antiflammatory drugs (NSAIDs).

The compounds of the present invention may be combined, for example, with known anti-hyperproliferative, cytostatic or cytotoxic substances for the treatment of cancerous diseases. In addition, the compounds according to the invention may also be employed in combination with radiotherapy and/or a surgical intervention.

As active compounds suitable for combinations, there may be mentioned by way of example:

131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, BAY 86-9766 (RDEA 119), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+oestrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, refametinib, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

Preferably, the present invention relates to medicaments comprising at least one compound according to the invention and one or more of the following active compounds, in particular for the treatment and/or prophylaxis of androgen receptor-dependent proliferative disorders:
LHRH (luteinizing hormone-releasing hormone) agonists,
LHRH (luteinizing hormone-releasing hormone) antagonists,
C(17,20)-lyase inhibitors,
5-α-reductase inhibitors type I,
5-α-reductase inhibitors type II,
mixed 5-α-reductase inhibitors type I/II,
α-radiation emitting radiopharmaceuticals for the treatment of bone metastases, such as radium-223 chloride,
cytostatics,
VEGF (vascular endothelial growth factor) kinase inhibitors,
antigestagens,
anti-oestrogens,
EGF antibodies,
oestrogens or
other androgen receptor antagonists,
poly (ADP-ribose) polymerase I inhibitors, or
bispecific T-cell engagers (BiTE) coupled to a cell surface protein such as, for example, prostate-specific membrane antigen (PSMA).

The invention also relates to pharmaceutical preparations comprising at least one compound of the general formula I (or physiologically acceptable addition salts thereof with organic or inorganic acids) and the use of these compounds for preparing medicaments, in particular for the indications mentioned above.

The compounds can be used for the indications mentioned above, both after oral and after parenteral administration.

The compounds according to the invention can have systemic and/or local action. For this purpose, they can be administered in a suitable way, for example orally, parenterally, pulmonarly, nasally, sublingually, lingually, buccally, rectally, dermally, transdermally, conjunctivally, otically or as an implant or stent.

For these routes of application, the compounds according to the invention can be administered in suitable dosage forms.

Dosage forms that function according to the prior art, with rapid and/or modified release of the compounds according to the invention, containing the compounds according to the invention in crystalline and/or amorphisized and/or dissolved form, are suitable for oral administration, for example tablets (uncoated or coated tablets, for example with enteric coatings or coatings with delayed dissolution or insoluble coatings, which control the release of the compound according to the invention), tablets that disintegrate rapidly in the oral cavity or films/wafers, films/lyophilisates, capsules (for example hard-gelatin or soft-gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of absorption (for example intramuscularly, subcutaneously, intracutaneously, percutaneously or intraperitoneally). Suitable dosage forms for parenteral administration are inter alia injection and infusion preparations in the form of solutions, suspensions, emulsions, lyophilisates or sterile powders.

Suitable dosage forms for the other routes of administration are, for example, pharmaceutical forms for inhalation (inter alia powder inhalers, nebulizers), nasal drops, solutions, and sprays; tablets for lingual, sublingual or buccal administration, films/wafers or capsules, suppositories, ear or eye preparations, vaginal capsules, aqueous suspensions (lotions, shaking mixtures), lipophilic suspensions, ointments, creams, transdermal therapeutic systems (such as, for example, patches), milk, pastes, foams, dusting powders, implants, intrauterine systems, vaginal rings or stents.

The compounds according to the invention can be converted into the stated dosage forms. This can take place in a manner that is known per se, by mixing with inert, non-toxic, pharmaceutically suitable auxiliaries. These auxiliaries include inter alia vehicles (for example microcrystalline cellulose, lactose, mannitol), solvents (for example liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (for example antioxidants such as, for example, ascorbic acid), colorants (for example inorganic pigments such as, for example, iron oxides) and taste and/or odour correctants.

The present invention further relates to medicinal products comprising at least one compound according to the invention, usually together with one or more inert, non-toxic, pharmaceutically suitable auxiliaries, and their use for the purposes stated above.

In the case of oral administration, the amount per day is from about 0.01 to 100 mg/kg of body weight. The amount of a compound of the general formula I to be administered varies over a wide range and can cover every effective amount. Depending on the condition to be treated and the method of administration, the amount of the compound administered can be 0.01-100 mg/kg of body weight per day.

Nevertheless, it may optionally be necessary to deviate from the stated amounts, mainly depending on body weight, route of administration, individual response to the active substance, type of preparation and time point or interval in which administration takes place. Thus, in some cases it may be sufficient to use less than the aforementioned minimum amount, whereas in other cases the stated upper limit must be exceeded. In the case of administration of relatively large amounts, it may be advisable to divide these into several individual doses throughout the day.

The percentages in the following tests and examples are, unless stated otherwise, percentages by weight; parts are parts by weight. Proportions of solvents, dilution ratios and information about concentration for liquid/liquid solutions relate in each case to volume.

LIST OF ABBREVIATIONS, CHEMISTRY

Abbreviations and Acronyms:

| | |
|---|---|
| DMF | N,N-dimethylformamide |
| DMSO | dimethyl sulphoxide |
| h | hour(s) |
| HPLC | high-pressure, high-performance liquid chromatography |
| LC-MS | liquid chromatography-coupled mass spectroscopy |
| ES-MS | electrospray mass spectroscopy |
| min | minute(s) |
| MS | mass spectroscopy |
| NMR | nuclear magnetic resonance spectroscopy |
| RT | room temperature |
| TFA | trifluoroacetic acid |
| THF | tetrahydrofuran |

Purification of the Compounds According to the Invention

In some cases the compounds according to the invention could be purified by preparative HPLC, for example using an autopurifier apparatus from Waters (detection of the compounds by UV detection and electrospray ionization) in combination with commercially available, prepacked HPLC columns (for example XBridge column (from Waters), C18, 5 μm, 30×100 mm). The solvent system used was acetonitrile/water with addition of formic acid. Further additives known to the person skilled in the art, such as, for example, ammonia, ammonium acetate or trifluoroacetic acid, may be used. Instead of acetonitrile, it is also possible to use, for example, methanol.

In some cases, the following method was used for preparative HPLC separation:

| | |
|---|---|
| System: | Waters auto purification system: pump 2545, sample manager 2767, CFO, DAD 2996, ELSD 2424, SQD |
| Column: | XBridge C18 5 μm 100 × 30 mm |
| Solvent: | A = $H_2O$ + 0.1% by volume formic acid (99%) |
| | B = Acetonitrile |
| Gradient: | 0-1 min 1% B, 1-8 min 1-99% B, 8-10 min 99% B |
| Flow rate: | 50 ml/min |
| Temperature: | RT |
| Injection: | 1 × 2.5 ml |
| Detection: | DAD scan range 210-400 nm |
| | MS ESI+, ESI−, scan range 160-1000 m/z |

Freeze-drying or vacuum centrifugation was used for removing the HPLC solvent mixture. If the resulting compounds are present as TFA salts or formate salts, they can be converted by standard laboratory procedures known to the person skilled in the art into the respective free bases.

In some cases, the compounds according to the invention could be purified by chromatography on silica gel. For this purpose, for example, prepacked silica gel cartridges (for example an ISOLUTE® Flash silica gel (Biotage, formerly Separtis) a flash chromatography silica gel cartridge, in combination with the a FLASHMASTER™ II (Argonaut/Biotage) chromatography system, and chromatography solvents or solvent mixtures such as, for example, hexane, ethyl acetate and dichloromethane and methanol were used.

Structural Analysis of the Compounds According to the Invention:

In some cases, the compounds according to the invention were analysed by LC-MS:

In some cases, the following analytical method was used:

Instrument: Waters Acquity UPLC-MS SQD; column: Acquity UPLC BEH C18 1.7 50×2.1 mm; mobile phase A: water+0.1% by volume of formic acid (99%), mobile phase B: acetonitrile; gradient: 0-1.6 min 1-99% B, 1.6-2.0 min 99% B; flow rate 0.8 ml/min; temperature: 60° C.; injection: 2 μl; DAD scan: 210-400 nm The following symbols are used in the NMR data of the compounds according to the invention:

| | |
|---|---|
| s | singlet |
| d | doublet |
| t | triplet |
| q | quartet |
| quin | quintet |
| m | multiplet |
| br | broad |
| mc | centred multiplet |

Synthesis of the Compounds According to the Invention:

Intermediate 1

17-Oxoestra-1,3,5(10)-trien-3-yl-1,1,2,2,3,3,4,4,4-nonafluorobutane-1-sulphonate

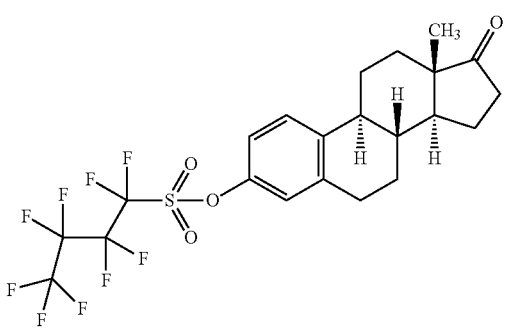

30.0 g (111 mmol) of oestrone and 46.0 g (222 mmol) of potassium carbonate were initially charged in 300 ml of THF. 40.2 g (133 mmol) of 1,1,2,2,3,3,4,4,4-nonafluorobutane-1-sulphonyl fluoride were added, and the mixture was stirred under reflux for 7 h and at RT for 18 h. Another 0.2 equivalents of 1,1,2,2,3,3,4,4,4-butane-1-sulphonyl fluoride were then added, and the mixture was heated under reflux for 4 h. The solid was filtered off and the filtrate was concentrated to half of its original volume, poured onto saturated sodium chloride solution and stirred for 35 min. The phases were then separated, the aqueous phase was extracted twice with ethyl acetate and the combined organic phases were washed with water and saturated sodium chloride solution and dried over sodium sulphate. The solvent was removed and the residue was triturated with hexane. This gave 63.6 g of a solid. $C_{22}H_{21}F_9O_4S$. $^1$H-NMR (300 MHz, DMSO-$d_6$): δ [ppm]=0.80 (s, 3H), 1.27-1.64 (m, 6H), 1.66-1.80 (m, 1H), 1.85-2.12 (m, 3H), 2.18-2.43 (m, 3H), 2.81-2.94 (m, 2H), 7.11-7.21 (m, 2H), 7.43 (d, 1H).

Intermediate 2

(E)-Ethyl 3-(17-oxoestra-1,3,5(10)-trien-3-yl)acrylate

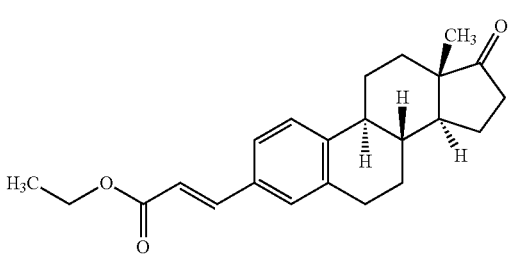

A mixture of 500 mg (0.91 mmol) of 17-oxoestra-1,3,5(10)-trien-3-yl-1,1,2,2,3,3,4,4,4-nonafluorobutane-1-sulphonate, 181 mg of ethyl acrylate, 144 microliters of triethylamine, 47 mg (0.15 mmol) of tri-2-tolylphosphine and 14 mg (0.06 mmol) of palladium(II) acetate in 8 ml of acetonitrile was heated in a microwave at 150° C./100 watt. The mixture was combined with two analogous reaction batches (in each case starting with 1 g of 17-oxoestra-1,3,5(10)-trien-3-yl-1,1,2,2,3,3,4,4,4-nonafluorobutane-1-sulphonate). The combined mixture was filtered through Celite, poured into aqueous ammonium chloride solution and stirred for 30 min. The mixture was extracted three times with dichloromethane, washed with saturated sodium chloride solution, dried over sodium sulphate and concentrated. Purification by column chromatography on silica gel (hexane/ethyl acetate) gave 287 mg of a solid. $C_{23}H_{28}O_3$. $^1$H-NMR (400 MHz, DMSO-$d_6$): δ [ppm]=0.80 (s, 3H), 1.21 (t, 3H), 1.28-1.45 (m, 3H), 1.45-1.60 (m, 3H), 1.69-1.80 (m, 1H), 1.87-2.10 (m, 3H), 2.18-2.29 (m, 1H), 2.32-2.45 (m, 2H), 2.79-2.88 (m, 2H), 4.14 (q, 2H), 6.51 (d, 1H), 7.29 (d, 1H), 7.39 (s, 1H), 7.41-7.45 (m, 1H), 7.54 (d, 1H).

Intermediate 3

Ethyl 3-(17-oxoestra-1,3,5(10)-trien-3-yl)propanoate

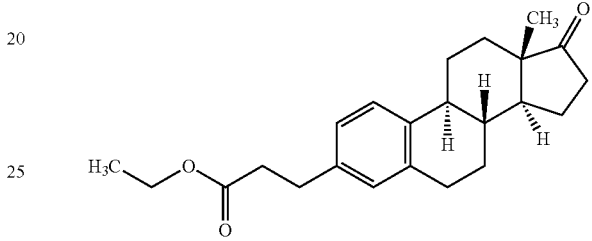

100 mg of Pd/carbon (10%) were added to 282 mg (0.80 mmol) of (E)-ethyl 3-(17-oxoestra-1,3,5(10)-trien-3-yl) acrylate in 10 ml of ethyl acetate. At RT, hydrogen was introduced for 1 h. The catalyst was filtered off and the residue was washed with a total of 10 ml of ethyl acetate. Removal of the solvent under reduced pressure gave 278 mg (98% of theory) of product. $C_{23}H_{30}O_3$.

1H-NMR (300 MHz, chloroform-d): δ [ppm]=0.90 (s, 3H), 1.25 (t, 3H), 1.35-1.73 (m, ), 1.91-2.21 (m, 4H), 2.23-2.34 (m, 1H), 2.35-2.56 (m, 2H), 2.60 (t, 2H), 2.84-2.97 (m, 4H), 4.14 (q, 2H), 6.95 (s, 1H), 7.00 (d, 1H), 7.22 (d, 1H).

Intermediate 4

Ethyl 3-(17-{[(trifluoromethyl)sulphonyl]oxy}estra-1,3,5(10),16-tetraen-3-yl)propanoate

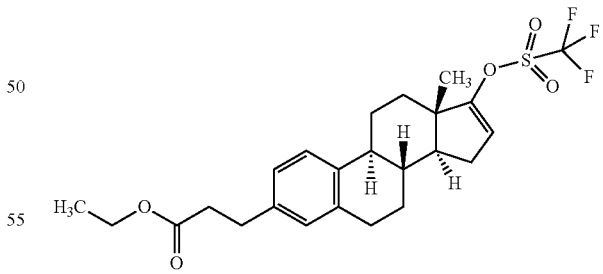

0.25 ml (1.16 mmol) of 2,6-di-tert-butylpyridine was added dropwise to a solution of 274 mg (0.77 mmol) of ethyl 3-(17-oxoestra-1,3,5(10)-trien-3-yl)propanoate in 10 ml of dichloromethane. 0.16 ml (0.93 mmol) of trifluoromethanesulphonic anhydride was then added dropwise, and the mixture was stirred at RT for 24 h. The mixture was poured carefully into 70 ml of saturated sodium bicarbonate solution, the phases were separated, the aqueous phase was extracted twice with dichloromethane and the combined organic phases were washed with saturated sodium bicarbonate solution, twice with 1M aqueous hydrochloric acid solution, sodium chloride solution, dried over sodium sulphate and concentrated. This gave 522 mg of a brown oil. $C_{24}H_{29}F_3O_5S$. $^1$H-NMR (400 MHz, chloroform-d, selected signals): δ [ppm]=1.00 (s, 3H). 1.25 (t, 3H), 1.80 (td, 1H), 1.85-1.98 (m, 2H), 2.04-2.17 (m, 1H), 2.25-2.47 (m, 3H), 2.55-2.67 (m), 2.79-2.96 (m), 4.14 (q, 2H), 5.58-5.67 (m, 1H), 6.95 (s, 1H), 7.00 (d, 1H), 7.19 (d, 1H).

Intermediate 5

Ethyl 3-(17-(5-fluoropyridin-3-yl)estra-1,3,5(10),16-tetraen-3-yl)propanoate

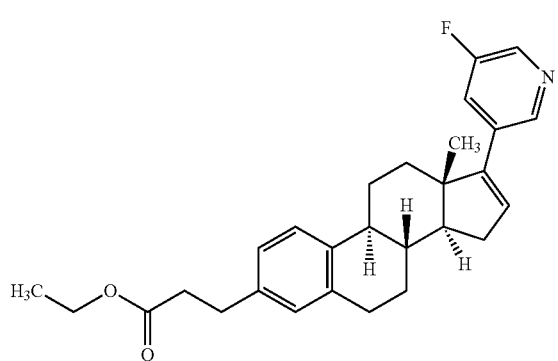

522 mg (1.07 mmol) of ethyl 3-[17-{[(trifluoromethyl)sulphonyl]oxy}estra-1,3,5(10),16-tetraen-3-yl]propanoate were initially charged in 5 ml of toluene and 3 ml of ethanol. 212 mg (1.4 equivalents) of 5-fluoropyridine-3-boronic acid, 91 mg of LiCl, 1.3 ml of 2M aqueous sodium carbonate solution and 38 mg of bis(triphenylphosphine)palladium(II) chloride were then added, and the mixture was heated in a microwave at 120° C./300 W for 90 min. The mixture was filtered, the phases were separated and the aqueous phase was extracted twice with in each case 20 ml of ethyl acetate. The combined organic phases were washed with saturated sodium bicarbonate solution and saturated sodium chloride solution, dried over sodium sulphate and concentrated. Purification by column chromatography on silica gel (hexane/ethyl acetate) gave 108 mg of a yellowish oil. $C_{28}H_{32}FNO_2$. $^1$H-NMR (300 MHz, CHLOROFORM-d): δ [ppm]=1.04 (s, 3H), 1.25 (t), 1.2-1.90 (m), 1.91-2.04 (m, 1H), 2.08-2.26 (m, 2H), 2.26-2.51 (m, 3H), 2.61 (t, 2H), 2.82-2.97 (m), 4.14 (q, 2H), 6.07-6.12 (m, 1H), 6.91-7.05 (m, 2H), 7.22 (d, 1H), 7.40 (dt, 1H), 8.34 (d, 1H), 8.45-8.51 (m, 1H).

Intermediate 6

Benzyl [(17-oxoestra-1,3,5(10)-trien-3-yl)oxy]acetate

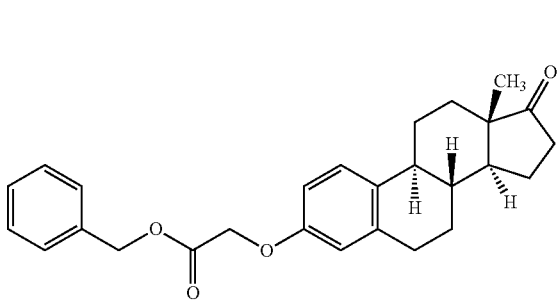

A mixture of 5.00 g (18 mmol) of oestrone, 3.5 ml of benzyl bromoacetate (22 mmol) and 7.67 g (55 mmol) of potassium carbonate and 70 ml of THF was heated under reflux overnight. Another 0.2 equivalent of benzyl bromoacetate was added, and the mixture was stirred under reflux for a further 3 h. Water was added to the reaction mixture. The phases were allowed to separated, and the aqueous phase was extracted twice with ethyl acetate. The combined org. phases were washed with water, saturated sodium chloride solution, dried over sodium sulphate, filtered and concentrated. Purification by column chromatography on silica gel (hexane/ethyl acetate) gave 7.91 g of a colourless oil. $C_{27}H_{30}O_4$. $^1$H-NMR (300 MHz, chloroform-d): δ [ppm]=0.91 (s, 3H), 1.35-1.73 (m), 1.90-2.59 (m), 2.78-2.96 (m, 2H), 4.64 (s, 2H), 5.24 (s, 2H), 6.60-6.67 (m, 1H), 6.70 (dd, 1H), 7.19 (d, 1H), 7.35 (s, 5H).

Intermediate 7

Benzyl [(17-{[(trifluoromethyl)sulphonyl]oxy}estra-1,3,5(10),16-tetraen-3-yl)oxy]acetate

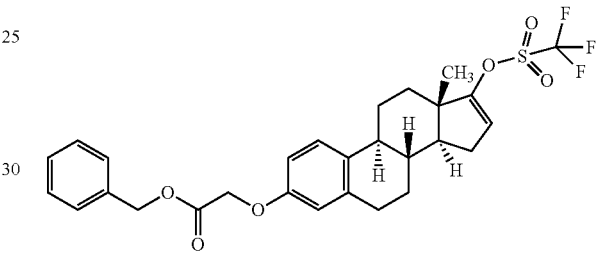

7.9 g (18.9 mmol) of benzyl [(17-oxoestra-1,3,5(10)-trien-3-yl)oxy]acetate were reacted analogously to the preparation of Intermediate 4 to give 10.1 g of the title compound as a crude product. $C_{24}H_{29}F_3O_6S$. $^1$H-NMR (400 MHz, DMSO-$d_6$): δ [ppm]=0.92 (s, 3H), 1.29-1.61 (m), 1.65-1.86 (m, 3H), 2.02-2.15 (m, 1H), 2.17-2.40 (m, 3H), 2.66-2.78 (m, 2H), 4.76 (s, 2H), 5.15 (s, 2H), 5.72 (d, 1H), 6.57 (d, 1H), 6.65 (dd, 1H), 7.10 (d, 1H), 7.27-7.41 (m, 5H).

Intermediate 8

17-(5-Fluoropyridin-3-yl)-3-methoxyestra-1,3,5(10),16-tetraene

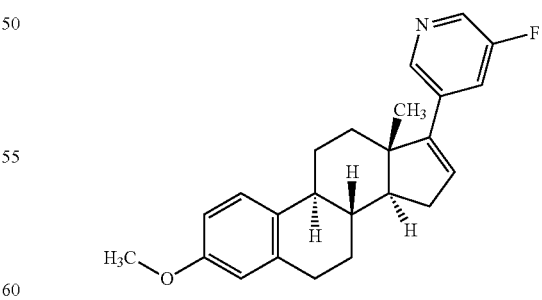

1.23 g (0.05 equiv.) of bis(triphenylphosphine)palladium (II) chloride were added to a mixture of 14.6 g (35.1 mmol) of 3-methoxyestra-1,3,5(10),16-tetraen-17-yltrifluoromethanesulphonate (S. Cacchi, E. Morera, Synthesis, 1986, 4, 320-322), 6.92 g (1.4 equiv.) of 5-fluoropyridine-3-boronic acid, 2.97 g (2.0 equiv.) of lithium chloride, 47 ml of 2M aqueous sodium carbonate solution, 80 ml of ethanol and 100 ml of toluene, and the mixture was heated under reflux for 4.5 h. The mixture was filtered through Celite, the phases were separated and the aqueous phase was extracted with ethyl acetate. The combined organic phases were washed with saturated aqueous sodium bicarbonate solution and sodium chloride solution, dried over sodium sulphate and concentrated. The residue was purified by column chromatography on silica gel (hexane/ethyl acetate). This gave 10.4 g (81% of theory) of a solid. $C_{24}H_{26}FNO$. $^1$H-NMR (300 MHz, chloroform-d): δ [ppm]=1.05 (s, 3H), 1.40-1.75 (m), 1.82 (td, 1H), 1.90-2.03 (m, 1H), 2.03-2.27 (m), 2.27-2.57 (m), 2.84-3.03 (m, 2H), 3.79 (s, 3H), 5.99-6.18 (m, 1H), 6.66 (d, 1H), 6.73 (dd, 1H), 7.21 (d, 1H), 7.40 (dt, 1H), 8.34 (d, 1H), 8.48 (s, 1H).

Intermediate 9

17-(5-Fluoropyridin-3-yl)estra-1,3,5(10),16-tetraen-3-ol

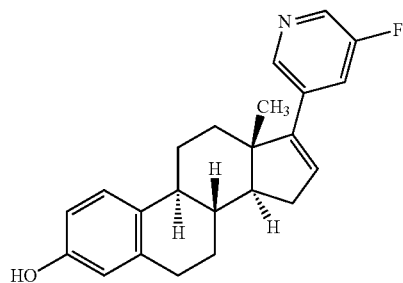

In a temperature range of from 0° C. to 3° C., 11.6 ml of 2,6-lutidine diluted with 50 ml of dichloromethane were added dropwise to 100 ml of a 1M solution of boron tribromide in dichloromethane. 10.4 g of 1745-fluoropyridin-3-yl)-3-methoxyestra-1,3,5(10),16-tetraene dissolved in 50 ml of dichloromethane were then added dropwise at from 0° C. to 3° C., and the mixture was allowed to warm to RT in an ice bath overnight. The reaction mixture was added to 400 ml of ice/water and stirred for 40 min. The phases were separated, the aqueous phases were extracted three times with in each case 50 ml of dichloromethane and the combined org. phases were washed with saturated sodium chloride solution, dried over sodium sulphate and concentrated. The crude product was triturated at 40° C. in hexane, filtered off with suction and washed with hexane. This gave 13.9 g of a brown solid (crude product). $C_{23}H_{24}FNO$. MS (ESIpos) mass found: 349.00.

1H-NMR (300 MHz, DMSO-d6): δ [ppm]=0.98 (s, 3H), 1.27-1.61 (m, 4H), 1.69 (td, 1H), 1.78-1.90 (m, 1H), 2.03-2.35 (m, 5H), 2.65-2.84 (m, 2H), 6.23-6.28 (m, 1H), 6.40-6.52 (m, 2H), 7.01 (d, 1H), 7.63-7.70 (m, 1H), 8.42 (d, 1H), 8.46-8.50 (m, 1H), 8.98 (s, 1H).

Intermediate 10

3-Methoxy-17-(3-pyridyl)estra-1,3,5(10),16-tetraene

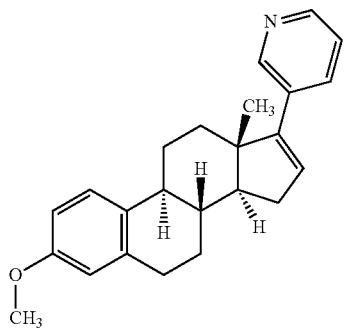

At 80° C., 3.00 g (7.20 mmol) of 3-methoxyestra-1,3,5(10),16-tetraen-17-yltrifluoromethanesulphonate were reacted analogously to Example 8 with 1.24 g (1.40 equiv.) of pyridine-3-boronic acid overnight analogously. This gave, after purification by column chromatography on silica gel (hexane/ethyl acetate), 1.2 g of the title compound as a crude product. 120 mg of the crude product were purified further by HPLC. This gave 60 mg of the title compound. $C_{24}H_{27}NO$. MS (ESIpos) mass found: 345.21. $^1$H-NMR (400 MHz, DMSO-d$_6$): δ [ppm]=0.98 (s, 3H), 1.32-1.61 (m, 4H), 1.71 (td, 1H), 1.83-1.91 (m, 1H), 2.04-2.14 (m, 2H), 2.17-2.38 (m, 3H), 2.75-2.89 (m, 2H), 3.66 (s, 3H), 6.11 (dd, 1H), 6.60 (d, 1H), 6.65 (dd, 1H), 7.13 (d, 1H), 7.29-7.34 (m, 1H), 7.76 (dt, 1H), 8.42 (dd, 1H), 8.59 (d, 1H).

Intermediate 11

17-(3-Pyridyl)estra-1,3,5(10),16-tetraen-3-ol

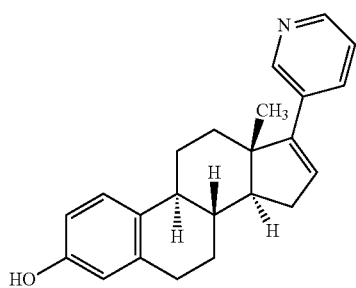

Analogously to the preparation of Intermediate 9, 1.1 g of 3-methoxy-17-(3-pyridyl)estra-1,3,5(10),16-tetraene were reacted with boron tribromide (1M in dichloromethane) and 2,6-lutidine. For work-up, the mixture was poured into ice-water and stirred. Dichloromethane was added. The solid that remained was filtered off with suction, washed with water and dichloroethane and dried by adding toluene followed by removal of the toluene on a rotary evaporator (three times). Trituration with diethyl ether and drying under reduced pressure gave 511 mg of the title compound. $C_{23}H_{25}NO$. MS (ESIpos) mass found: 332.00. $^1$H-NMR (400 MHz, DMSO-d$_6$): δ [ppm]=1.01 (s, 3H), 1.31-1.61 (m, 4H), 1.72 (td, 1H), 1.85 (dt, 1H), 2.09-2.23 (m, 3H), 2.27-2.41 (m, 2H), 2.66-2.83 (m, 2H), 6.40-6.45 (m, 2H), 6.49 (dd, 1H), 7.02 (d, 1H), 7.84 (dd, 1H), 8.37-8.42 (m, 1H), 8.67 (d, 1H), 8.82 (s, 1H).

PREPARATION OF THE EXAMPLE COMPOUNDS

Example 1

3-[17-(5-Fluoropyridin-3-yl)estra-1,3,5(10),16-tetraen-3-yl]propanoic acid

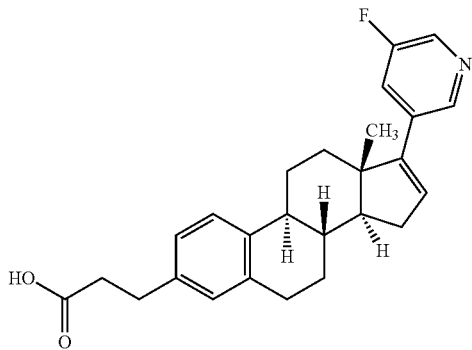

A mixture of 100 mg (0.23 mmol) of ethyl 3-[17-(5-fluoropyridin-3-yl)estra-1,3,5(10),16-tetraen-3-yl]propanoate, 3 ml of THF, 0.5 ml of ethanol and 0.58 ml of 2M aqueous sodium hydroxide solution was stirred at RT overnight and then diluted with water and adjusted to a pH of 3 using a 10% strength aqueous citric acid solution. The aqueous phase was extracted three times with ethyl acetate. The combined organic phases were dried over sodium sulphate and concentrated. The residue was purified by preparative HPLC (acetonitrile/water/formic acid). This gave 44 mg of a white solid. $C_{26}H_{28}FNO_2$. MS (ESIpos) mass found: 405.21. $^1$H-NMR (300 MHz, DMSO-d$_6$): δ [ppm]=0.99 (s, 3H), 1.24-1.62 (m, 4H), 1.62-1.78 (m, 1H), 1.78-1.96 (m, 1H), 2.01-2.40 (m, 5H), 2.70 (t, 2H), 2.75-2.93 (m, 2H), 6.26 (s., 1H), 6.85-6.96 (m, 2H), 7.13 (d, 1H), 7.68 (d, 1H), 8.43 (d, 1H), 8.48 (s, 1H)., 12.1 (s).

Example 2

({17-[5-(Trifluoromethyl)pyridin-3-yl]estra-1,3,5(10),16-tetraen-3-yl}oxy)acetic acid

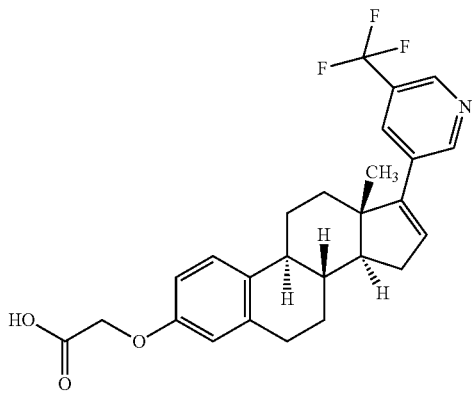

200 mg (0.36 mmol) benzyl {[17-{[(trifluoromethyl)sulphonyl]oxy}estra-1,3,5(10),16-tetraen-3-yl]oxy}acetate were initially charged in 1.5 ml of toluene and 1 ml of ethanol. 97 mg (1.4 equivalents) of 5-(trifluoromethyl)pyridine-3-boronic acid, 31 mg of LiCl, 0.49 ml of 2M aqueous sodium carbonate solution and 12 mg of 1,3-bis(2,6-diisopropylphenyl)imidazol-2-ylidene(3-chloropyridyl)palladium(II) dichloride (CAS 905459-27-0) were then added, and the mixture was heated in a microwave at 120° C./300 W for 90 min. The mixture was filtered, 0.90 ml of 2 M aqueous sodium hydroxide solution was added and the mixture was heated in a microwave at 120° C./300 W for 30 min. The reaction mixture was adjusted to a pH of 3 using 10% strength aqueous citric acid solution and the aqueous phase was extracted three times with ethyl acetate. The combined organic phases were washed with saturated sodium chloride solution, dried over sodium sulphate and concentrated. Purification by preparative HPLC (acetontrile/water/formic acid) gave 43 mg of a solid. $C_{26}H_{26}F_3NO_3$. MS (ESIpos) mass found: 457.19. 1H-NMR (300 MHz, DMSO-d6): δ [ppm]=1.00 (s, 3H), 1.27-2.41 (m), 2.70-2.88 (m, 2H), 4.56 (s, 2H), 6.35 (s., 1H), 6.46-6.73 (m, 2H), 7.13 (d, 1H), 8.03 (s., 1H), 8.83 (s, 1H), 8.90 (s, 1H), 12.9 (s).

Example 3

{[17-(5-Fluoropyridin-3-yl)estra-1,3,5(10),16-tetraen-3-yl]oxy}acetic acid

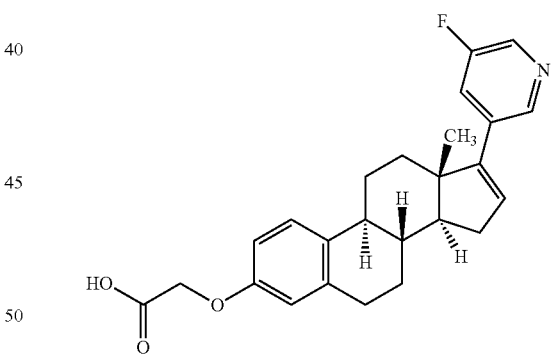

Analogously to the preparation of Example 2, 200 mg (0.36 mmol) of benzyl {[17-{[(trifluoromethyl)sulphonyl]oxy}estra-1,3,5(10),16-tetraen-3-yl]oxy}acetate were reacted with 72 mg (0.51 mmol) of 5-fluoropyridine-3-boronic acid. This gave 31 mg (21% of theory) of a solid. $C_{25}H_{26}FNO_3$. MS (ESIpos) mass found: 407.19. 1H-NMR (300 MHz, DMSO-d6): δ [ppm]=0.98 (s, 3H), 1.26-1.63 (m, 4H), 1.64-1.78 (m, 1H), 1.79-1.93 (m, 1H), 2.00-2.39 (m, 5H), 2.73-2.89 (m, 2H), 4.56 (s, 2H), 6.26 (s., 1H), 6.53-6.66 (m, 2H), 7.13 (d, 1H), 7.68 (dd, 1H), 8.42 (d, 1H), 8.48 (s, 1H), 12.9 (s).

Example 4

{[17-(6-Methylpyridin-3-yl)estra-1,3,5(10),16-tetraen-3-yl]oxy}acetic acid

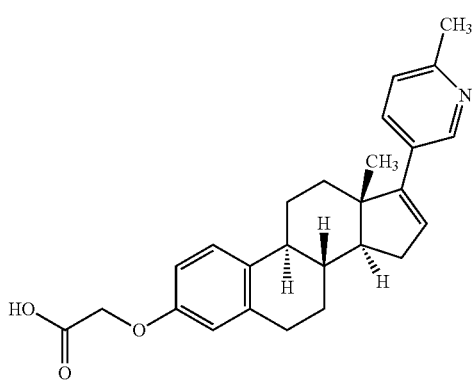

9.6 mg of bis(triphenylphosphine)palladium(II) chloride were added to a mixture of 150 mg of benzyl [(17-{[(trifluoromethyl)sulphonyl]oxy}estra-1,3,5(10),16-tetraen-3-yl)oxy]acetate, 52 mg (1.4 equiv.) of 2-methyl-5-boronic acid, 23 mg (2.0 equiv.) of lithium chloride in 1.5 ml of toluene, 1 ml of ethanol and 0.37 ml 2M aqueous sodium carbonate solution, and the mixture was stirred at 100° C. overnight. 0.7 ml of 2M aqueous sodium hydroxide solution was added, and the mixture was stirred at 100° C. overnight. The reaction mixture was diluted with water, adjusted to pH=4 with citric acid solution and extracted three times with ethyl acetate. The combined organic phases were concentrated and purified by preparative HPLC. This gave 24 mg of the title compound. $C_{26}H_{29}NO_3$. MS (ESIpos) mass found: 403.21. $^1$H-NMR (300 MHz, DMSO-d$_6$): δ [ppm]=0.96 (s, 3H), 1.29-1.62 (m, 4H), 1.69 (td, 1H), 1.80-1.92 (m, 1H), 1.99-2.39 (m, 6H), 2.41 (s, 3H), 2.71-2.89 (m, 2H), 4.56 (s, 2H), 6.00-6.07 (m, 1H), 6.56 (d, 1H), 6.59-6.66 (m, 1H), 7.10-7.22 (m, 2H), 7.61-7.68 (m, 1H), 8.44 (d, 1H), 12.9 (br. s, 1H).

Example 5

{[17-(Pyrimidin-5-yl)estra-1,3,5(10),16-tetraen-3-yl]oxy}acetic acid

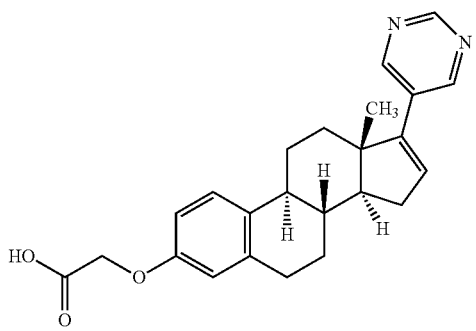

Analogously to Example 4, 150 mg of benzyl [(17-{[(trifluoromethyl)sulphonyl]oxy}estra-1,3,5(10),16-tetraen-3-yl)oxy]acetate were reacted with 47 mg of pyrimidine-5-boronic acid. Purification by preparative HPLC gave 42 mg of the title compound. $C_{24}H_{26}N_2O_3$. MS (ESIpos) mass found: 390.19. $^1$H-NMR (400 MHz, DMSO-d$_6$): δ [ppm]=0.98 (s, 3H), 1.33-1.62 (m, 4H), 1.72 (td, 1H), 1.83-1.91 (m, 1H), 2.08-2.16 (m, 2H), 2.18-2.38 (m, 3H), 2.62-2.65 (m, 1H), 2.73-2.87 (m, 2H), 4.55 (s, 2H), 6.27-6.31 (m, 1H), 6.57 (d, 1H), 6.63 (dd, 1H), 7.13 (d, 1H), 8.82 (s, 2H), 9.04 (s, 1H).

Example 6

5-[3-(Carboxymethoxy)estra-1,3,5(10),16-tetraen-17-yl]nicotinic acid

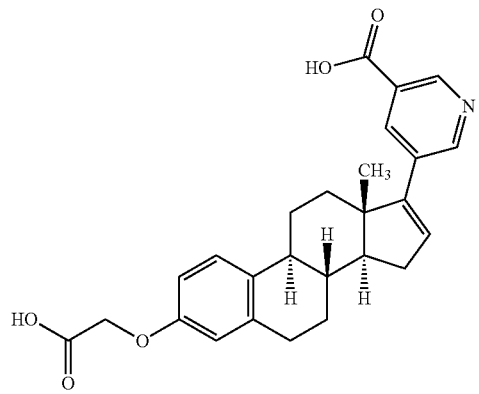

Analogously to Example 4, 150 mg of benzyl [(17-{[(trifluoromethyl)sulphonyl]oxy}estra-1,3,5(10),16-tetraen-3-yl)oxy]acetate were reacted with 100 mg of methyl 5-(4,4,5,5-tetramethyl-1,3,2-dioxaborolan-2-yl)nicotinate. Purification by preparative HPLC and trituration of the solid obtained with diethyl ether gave 39 mg of the title compound. $C_{26}H_{27}NO_5$. MS (ESIpos) mass found: 433.19. $^1$H-NMR (300 MHz, DMSO-d$_6$): δ [ppm]=0.99 (s, 3H), 1.30-1.63 (m, 5H), 1.63-1.79 (m, 1H), 1.82-1.93 (m, 1H), 2.04-2.40 (m, 6H), 2.73-2.85 (m, 2H), 4.56 (s, 2H), 6.23-6.27 (m, 1H), 6.57 (d, 1H), 6.63 (dd, 1H), 7.13 (d, 1H), 8.16 (t, 1H), 8.81 (d, 1H), 8.91 (d, 1H), 13.2 (br. s).

Example 7

{[17-(6-Methylpyridazin-4-yl)estra-1,3,5(10),16-tetraen-3-yl]oxy}acetic acid

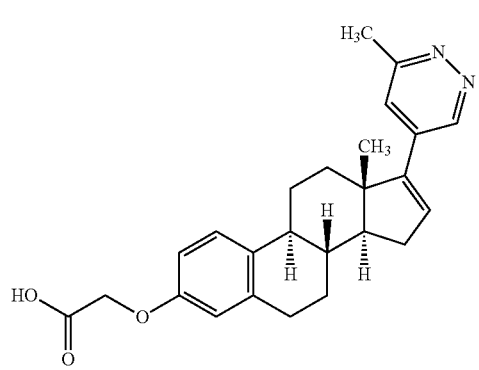

Analogously to Example 4, 181 mg (0.33 mmol) of benzyl [(17-{[(trifluoromethyl)sulphonyl]oxy}estra-1,3,5(10),16-tetraen-3-yl)oxy]acetate were reacted with 101 mg (0.46 mmol) of 3-methyl-5-(4,4,5,5-tetramethyl-1,3,2-dioxaborolan-2-yl)pyridazine. Purification by preparative HPLC gave a crude product which was triturated with diethyl ether and with ethyl acetate. This gave 14 mg (9% of theory) of the title compound. $C_{25}H_{28}N_2O_3$. MS (ESIpos) mass found: 404.21. $^1$H-NMR (400 MHz, DMSO-$d_6$): δ [ppm]=1.01 (s, 3H), 1.32-1.61 (m, 4H), 1.69 (td, 1H), 1.82-1.90 (m, 1H), 2.08-2.38 (m, 5H), 2.58 (s, 3H), 2.71-2.88 (m, 2H), 4.51 (s, 2H), 6.54-6.58 (m, 2H), 6.62 (dd, 1H), 7.13 (d, 1H), 7.48 (d, 1H), 9.10 (d, 1H).

Example 8

3-{[17-(5-Fluoropyridin-3-yl)estra-1,3,5(10),16-tetraen-3-yl]oxy}-2,2-dimethylpropanoic acid

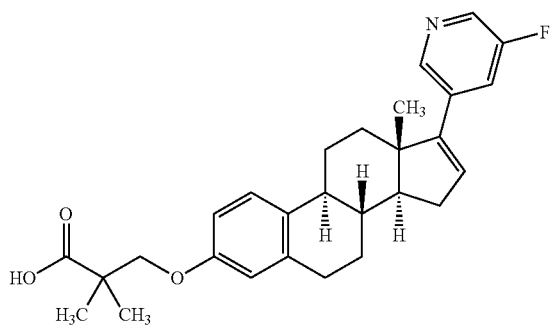

A mixture of 120 mg (0.31 mmol) of 17-(5-fluoropyridin-3-yl)estra-1,3,5(10),16-tetraen-3-ol, 61 mg (0.37 mmol, 1.2 equiv.) of methyl 3-chloro-2,2-dimethylpropanoate, 212 mg (1.53 mmol, 5.0 equiv.) of potassium carbonate and 5 mg of potassium iodide in 4.6 ml of DMSO was stirred at 80° C. for 18 h. 0.77 ml of 2M aqueous sodium hydroxide solution was added, and the mixture was stirred at RT overnight. The mixture was diluted with water, adjusted to a pH of 3-4 with 10 percent strength aqueous citric acid solution and extracted three times with ethyl acetate, the extracts were concentrated and the residue was purified by preparative HPLC. This gave 7 mg of a solid. $C_{28}H_{32}FNO_3$. MS (ESIpos) mass found: 449.24. $^1$H-NMR (400 MHz, DMSO-$d_6$): δ [ppm]=0.98 (s, 3H), 1.16 (s, 6H), 1.31-1.61 (m, 4H), 1.65-1.76 (m, 1H), 1.81-1.92 (m, 1H), 2.05-2.38 (m, 5H), 2.75-2.84 (m, 2H), 3.85 (s, 2H), 6.24-6.28 (m, 1H), 6.59 (d, 1H), 6.64 (dd, 1H), 7.12 (d, 1H), 7.67 (dt, 1H), 8.43 (d, 1H), 8.49 (t, 1H), 12.3 (s).

Example 9

4-{[17-(5-Fluoropyridin-3-yl)estra-1,3,5(10),16-tetraen-3-yl]oxy}butanoic acid

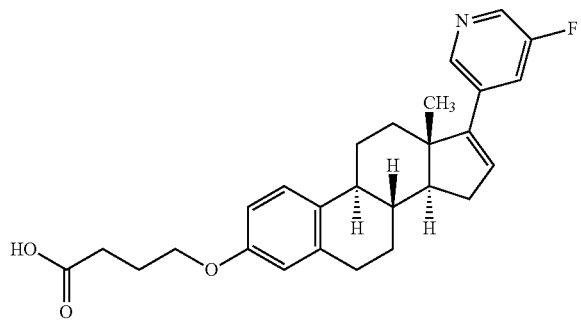

A mixture of 100 mg (0.29 mmol) of 17-(5-fluoropyridin-3-yl)estra-1,3,5(10),16-tetraen-3-ol, 78 mg (0.43 mmol, 1.2 equiv.) of methyl 4-bromobutanoate, 198 mg (1.53 mmol, 5.0 equiv.) of potassium carbonate and 4 mg of sodium iodide was stirred at 80° C. for 18 h. Another 78 mg of methyl 4-bromobutyrate were then added, and the mixture was stirred at 120° C. overnight. 0.72 ml of 2M aqueous sodium hydroxide solution was added, and the mixture was stirred at 40° C. for 3 h. The mixture was diluted with water, adjusted to a pH of 4 with 10 percent strength aqueous citric acid solution and extracted three times with ethyl acetate, the extracts were concentrated and the residue was purified by preparative HPLC. This gave 43 mg of a solid. $C_{27}H_{30}FNO_3$. MS (ESIpos) mass found: 435.22. $^1$H-NMR (400 MHz, DMSO-$d_6$): δ [ppm]=0.99 (s, 3H), 1.31-1.61 (m, 4H), 1.71 (td, 1H), 1.82-1.92 (m, 3H), 2.06-2.37 (m, 7H), 2.77-2.84 (m, 2H), 3.89 (t, 2H), 6.25 (dd, 1H), 6.57-6.81 (m, 1H), 6.62-6.68 (m, 1H), 7.12 (d, 1H), 7.64-7.70 (m, 1H), 8.43 (d, 1H), 8.48 (t, 1H), 12.1 (br. s, 1H).

Example 10

(RS)-2-{[17-(5-Fluoropyridin-3-yl)estra-1,3,5(10),16-tetraen-3-yl]oxy}propanoic acid

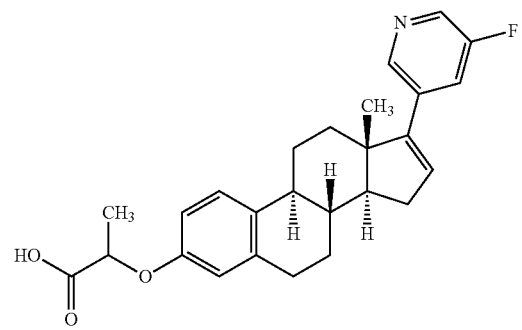

Analogously to Example 8, 100 mg of 17-(5-fluoropyridin-3-yl)estra-1,3,5(10),16-tetraen-3-ol were reacted with 117 mg (3.0 equiv.) of ethyl 2-chloropropanoate at 80° C. overnight. After addition of 2M aqueous sodium hydroxide solution, the mixture was stirred at 40° C. for 2.5 h. This gave, after preparative HPLC, 44 mg of the title compound.

$C_{26}H_{28}FNO_3$. MS (ESIpos) mass found: 421.21. $^1$H-NMR (300 MHz, DMSO-$d_6$): δ [ppm]=0.98 (s, 3H), 1.29-1.62 (m, 8H), 1.70 (td, 1H), 1.79-1.92 (m, 1H), 2.02-2.38 (m, 6H), 2.67-2.86 (m, 2H), 4.70 (q, 1H), 6.26 (br. s., 1H), 6.49-6.63 (m, 2H), 7.12 (d, 1H), 7.67 (dt, 1H), 8.43 (d, 1H), 8.47-8.50 (m, 1H), 12.9 (br. s, 1H).

Example 11

(RS)-2-{[17-(5-Fluoropyridin-3-yl)estra-1,3,5(10),16-tetraen-3-yl]oxy}butanoic acid

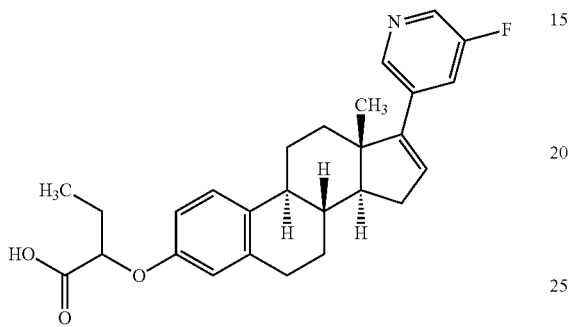

Analogously to Example 8, 100 mg of 17-(5-fluoropyridin-3-yl)estra-1,3,5(10),16-tetraen-3-ol were reacted with 117 mg (3.0 equiv.) of methyl 2-chlorobutanoate at 80° C. for 7 h and at room temperature for 72 h. After addition of 2M aqueous sodium hydroxide solution, the mixture was stirred at 40° C. for 5.5 h. This gave, after preparative HPLC, 48 mg of the title compound. $C_{27}H_{30}FNO_3$. MS (ESIpos) mass found: 435.22. $^1$H-NMR (400 MHz, DMSO-$d_6$): δ [ppm]=0.95 (t, 3H), 0.99 (s, 3H), 1.31-1.61 (m, 4H), 1.63-1.92 (m, 4H), 2.09-2.37 (m, 5H), 2.69-2.89 (m, 2H), 4.48-4.55 (m, 1H), 6.22-6.28 (m, 1H), 6.52-6.56 (m, 1H), 6.57-6.63 (m, 1H), 7.12 (d, 1H), 7.64-7.69 (m, 1H), 8.42 (d, 1H), 8.48 (t, 1H), 12.87 (br. s., 1H).

Example 12

(RS)-2-{[17-(5-Fluoropyridin-3-yl)estra-1,3,5(10),16-tetraen-3-yl]oxy}-3-methoxy-propanoic acid

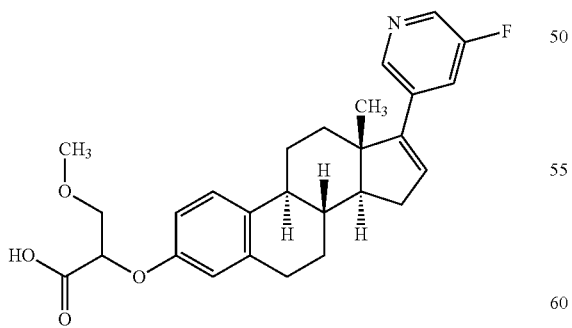

Analogously to Example 8, 100 mg of 17-(5-fluoropyridin-3-yl)estra-1,3,5(10),16-tetraen-3-ol were reacted with 169 mg (3.0 equiv.) of methyl 2-bromo-3-methoxypropanoate at 80° C. for 4 h. After addition of 2M aqueous sodium hydroxide solution, the mixture was stirred at 40° C. for 5.5 h. This gave, after preparative HPLC, 57 mg of the title compound. $C_{27}H_{30}FNO_4$. MS (ESIpos) mass found: 451.22. $^1$H-NMR (400 MHz, DMSO-$d_6$): δ [ppm]=0.99 (s, 3H), 1.32-1.61 (m, 4H), 1.71 (td, 1H), 1.81-1.92 (m, 1H), 2.05-2.37 (m, 5H), 2.71-2.87 (m, 2H), 3.28 (s, 3H), 3.66-3.78 (m, 2H), 4.79-4.84 (m, 1H), 6.24-6.27 (m, 1H), 6.54-6.59 (m, 1H), 6.62 (dt, 1H), 7.12 (d, 1H), 7.67 (dt, 1H), 8.42 (d, 1H), 8.48 (t, 1H), 13.01 (br. s., 1H).

Example 13

(RS)-2-{[17-(3-Pyridyl)estra-1,3,5(10),16-tetraen-3-yl]oxy}propanoic acid

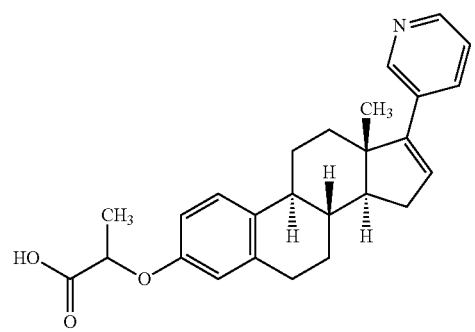

Analogously to Example 8, 100 mg of 17-(3-pyridyl)estra-1,3,5(10),16-tetraen-3-ol were reacted with 123 mg (3.0 equiv.) of ethyl 2-chloropropanoate at 80° C. overnight. After addition of 2M aqueous sodium hydroxide solution, the mixture was stirred at 40° C. for 4 h. This gave, after preparative HPLC, 19 mg of the title compound. $C_{26}H_{29}NO_3$. MS (ESIpos) mass found: 403.21. $^1$H-NMR (400 MHz, DMSO-$d_6$): δ [ppm]=0.98 (s, 3H), 1.31-1.61 (m, 7H, contains doublet at 1.43 ppm), 1.71 (td, 1H), 1.81-1.92 (m, 1H), 2.02-2.15 (m, 2H), 2.15-2.38 (m, 3H), 2.69-2.89 (m, 2H), 4.70 (qd, 1H), 6.11 (dd, 1H), 6.51-6.55 (m, 1H), 6.59 (dt, 1H), 7.12 (d, 1H), 7.29-7.34 (m, 1H), 7.76 (dt, 1H), 8.41 (dd, 1H), 8.58 (d, 1H), 12.9 (br. s., 1H).

Example 14

(RS)-2-{[17-(5-Fluoropyridin-3-yl)estra-1,3,5(10),16-tetraen-3-yl]oxy}propanamide

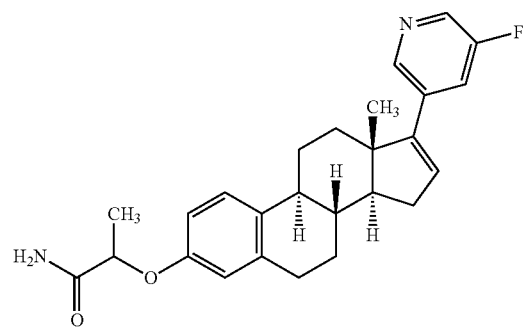

A mixture of 100 mg of 17-(5-fluoropyridin-3-yl)estra-1,3,5(10),16-tetraen-3-ol, 92 mg (3.0 equiv.) of 2-chloropropanamide, 198 mg (5 equiv.) of potassium carbonate and 4 mg of sodium iodide in 3 ml DMSO was stirred at 80° C. for 18 h, then at 100° C. for 4 h and at 120° C. for 18 h. The mixture was diluted with water and extracted three times with ethyl acetate, and the combined organic phases were dried over sodium sulphate and concentrated. Purification of the residue by preparative HPLC gave 18 mg of the title compound.

Purification Method Preparative HPLC:

| | |
|---|---|
| System: | Waters Autopurification system: Pump 254, Sample Manager 2767, CFO, DAD 2996, ELSD 2424, SQD 3100 |
| Column: | XBrigde C18 5 μm 100 × 30 mm |
| Solvent: | A = water + 0.1% vol. HCOOH (99%) |
| | B = acetonitrile |
| Gradient: | 0-8 min 50-90% B |
| Flow rate: | 50 ml/min |
| Temperature: | RT |
| Detection: | DAD scan range 210-400 nm |
| | MS ESI+, ESI−, scan range 160-1000 m/z |
| | ELSD |

| Fractions | Rt in min | purity in % | amount in mg | peak assignment |
|---|---|---|---|---|
| Example 14 | 4.4-4.7 | 98.6 | 18 | 8-1.41 min |
| Work-up: | The fractions were evaporated, tBuOH was added, the fractions were frozen at −65° C. and then freeze-dried. | | | |

$C_{26}H_{29}FN_2O_2$. MS (ESIpos) mass found: 420.22. $^1$H-NMR (400 MHz, DMSO-$d_6$): δ [ppm]=0.99 (s, 3H), 1.31-1.61 (m, 7H, contains doublet at 1.37 ppm), 1.71 (td, 1H), 1.87 (dt, 1H), 2.06-2.38 (m, 5H), 2.70-2.89 (m, 2H), 4.51 (q, 1H), 6.24-6.27 (m, 1H), 6.58 (t, 1H), 6.64 (dt, 1H), 7.10-7.18 (m, 2H), 7.36 (d, 1H), 7.63-7.71 (m, 1H), 8.43 (d, 1H), 8.46-8.51 (m, 1H).

Example 15

3-{[17-(5-Fluoropyridin-3-yl)estra-1,3,5(10),16-tetraen-3-yl]oxy}propan-1-ol

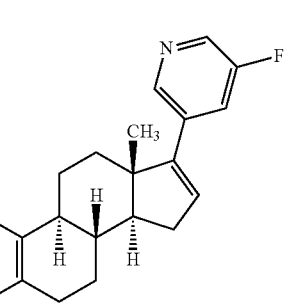

A mixture of 100 mg of 17-(5-fluoropyridin-3-yl)estra-1,3,5(10),16-tetraen-3-ol, 119 mg (3.0 equiv.) of 3-bromopropan-1-ol, 198 mg (5 equiv.) of potassium carbonate and 4 mg of sodium iodide in 3 ml of DMSO was stirred at 80° C. for 18 h, then at 100° C. for 4 h. The mixture was diluted with water and extract three times with ethyl acetate, and the combined organic phases were dried over sodium sulphate and concentrated. Purification of the residue by preparative HPLC gave 42 mg of the title compound. $C_{26}H_{30}FNO_2$. MS (ESIpos) mass found: 407.23. $^1$H-NMR (300 MHz, DMSO-$d_6$): δ [ppm]=0.98 (s, 3H), 1.29-1.62 (m, 4H), 1.64-1.91 (m, 4H), 2.03-2.39 (m, 5H), 2.71-2.90 (m, 2H), 3.44-3.55 (m, 2H), 3.93 (t, 2H), 4.48 (t, 1H), 6.23-6.28 (m, 1H), 6.59 (d, 1H), 6.64 (dd, 1H), 7.11 (d, 1H), 7.67 (dt, 1H), 8.43 (d, 1H), 8.46-8.51 (m, 1H).

Example 16

3-{[17-(5-Fluoropyridin-3-yl)estra-1,3,5(10),16-tetraen-3-yl]oxy}-2,2-dimethylpropan-1-ol

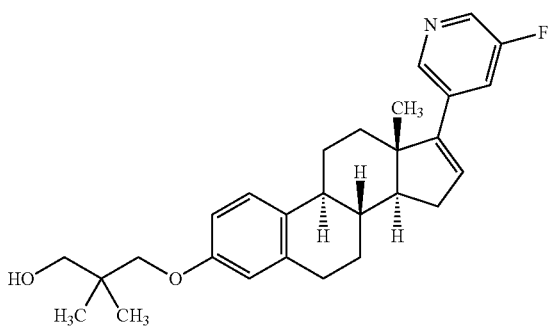

A mixture of 100 mg of 17-(5-fluoropyridin-3-yl)estra-1,3,5(10),16-tetraen-3-ol, 143 mg (3.0 equiv.) of 3-bromo-2,2-dimethylpropan-1-ol, 198 mg (5 equiv.) of potassium carbonate and 4 mg of sodium iodide in 3 ml of DMSO was stirred at 80° C. for 18 h, then at 100° C. for 4 h, at 120° C. for 18 h and at 150° C. for 5 h. The mixture was diluted with water and extracted three times with ethyl acetate, and the combined organic phases were dried over sodium sulphate and concentrated. Purification of the residue by preparative HPLC gave 42 mg of the title compound. $C_{28}H_{34}FNO_2$. MS (ESIpos) mass found: 435.26. $^1$H-NMR (400 MHz, DMSO-$d_6$): δ [ppm]=0.87 (s, 6H), 0.99 (s, 3H), 1.31-1.61 (m, 4H), 1.71 (td, 1H), 1.83-1.91 (m, 1H), 2.06-2.37 (m, 5H), 2.73-2.87 (m, 2H), 3.23 (d, 2H), 3.60 (s, 2H), 4.52 (t, 1H), 6.26 (dd, 1H), 6.59 (d, 1H), 6.64 (dd, 1H), 7.11 (d, 1H), 7.64-7.70 (m, 1H), 8.43 (d, 1H), 8.48 (t, 1H).

Example 17

(RS)-3-{[17-(5-Fluoropyridin-3-yl)estra-1,3,5(10),16-tetraen-3-yl]oxy}propan-1,2-diol

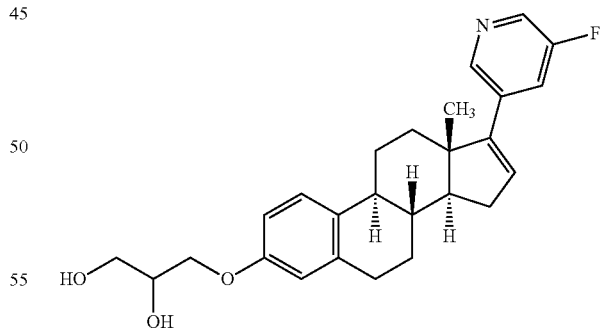

A mixture of 150 mg of 17-(5-fluoropyridin-3-yl)estra-1,3,5(10),16-tetraen-3-ol, 143 mg (3.0 equiv.) of 3-bromo-2,2-dimethylpropan-1-ol, 296 mg (5 equiv.) of potassium carbonate and 7 mg of potassium iodide in 3 ml of DMSO was stirred at 120° C. for 18 h. The mixture was diluted with water and extracted three times with ethyl acetate, and the combined organic phases were dried over sodium sulphate and concentrated. Purification of the residue by preparative HPLC gave 26 mg of the title compound. $C_{26}H_{30}FNO_3$. MS (ESIpos) mass found: 435.26. $^1$H-NMR (300 MHz, DMSO-d$_6$): δ [ppm]=0.99 (s, 3H), 1.30-1.62 (m, 4H), 1.71 (td, 1H), 1.81-1.93 (d, 1H), 2.02-2.39 (m, 5H), 2.74-2.86 (m, 2H), 3.39 (t, 2H), 3.67-3.80 (m, 2H), 3.90 (dd, 1H), 4.57 (t, 1H), 4.83 (d, 1H), 6.26 (br. s., 1H), 6.55-6.71 (m, 2H), 7.12 (d, 1H), 7.67 (dt, 1H), 8.40-8.52 (m, 2H).

Example 18

(RS)-{[17-(5-Fluoropyridin-3-yl)estra-1,3,5(10),16-tetraen-3-yl]oxy}(phenyl)acetic acid

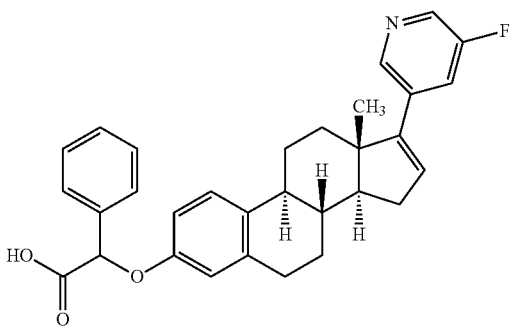

A mixture of 100 mg of 17-(5-fluoropyridin-3-yl)estra-1,3,5(10),16-tetraen-3-ol, 170 mg of ethyl chloro(phenyl)acetate (3 equiv.), 197 mg (5 equiv.) of potassium carbonate and 4 mg of sodium iodide in 3 ml of DMSO was stirred at 80° C. for 3 days. 0.7 ml of 2M aqueous sodium hydroxide solution was then added, and the mixture was stirred at 40° C. for 5.5 h. The reaction mixture was diluted with water, acidified to pH=4 with 10 percent strength citric acid solution and extracted three times with ethyl acetate. The combined organic phases were dried and concentrated. Purification by preparative HPLC gave 19 mg of the title compound.

Purification Method Preparative HPLC:

| | |
|---|---|
| System: | Agilent: Prep 1200, 2 × Prep Pump, DLA, MWD, Prep FC, |
| Column: | XBrigde C18 5 μm 100 × 30 mm |
| Solvent: | A = water + 0.1% TFA |
| | B = acetonitrile |
| Gradient: | 0-17.5 min 65-100% B, 17.5-20 min 100% B |
| Flow rate: | 38 ml/min |
| Temperature: | RT |
| Detection: | UV 254 nm |
| Fractions: | |
| Example 18 | 6.1-6.7 min    96%    19 mg    peak 12.2 min |
| Work-up: | The fractions were evaporated and then freeze-dried. |

$C_{31}H_{30}FNO_3$.MS (ESIpos) mass found: 483.22. 1H-NMR (300 MHz, DMSO-d6): δ [ppm]=0.98 (s, 3H), 1.30-1.63 (m, 4H), 1.70 (td, 1H), 1.81-1.91 (m, 1H), 2.04-2.38 (m, 5H), 2.74-2.84 (m, 2H), 5.71 (s, 1H), 6.23-6.27 (m, 1H), 6.63-6.73 (m, 2H), 7.14 (d, 1H), 7.32-7.42 (m, 3H), 7.48-7.54 (m, 2H), 7.64-7.70 (m, 1H), 8.42 (d, 1H), 8.48 (s, 1H), 13.1 (br. s., 1H).

Example 19

N-Ethyl-2-({17-[5-(trifluoromethyl)pyridin-3-yl]estra-1,3,5(10),16-tetraen-3-yl}oxy)acetamide

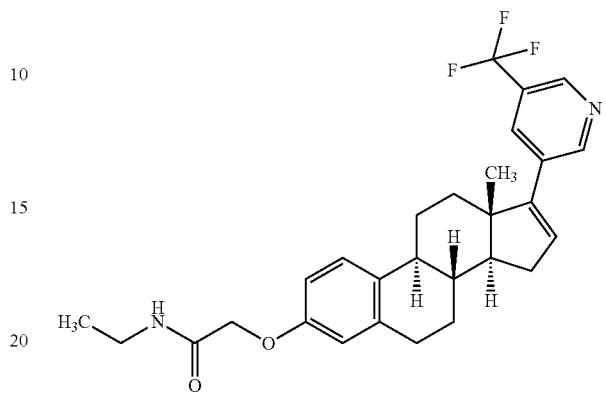

66 mg (3 equiv.) of 1,1'-carbonyldiimidazole and 7 mg of imidazole hydrochloride were added to 62 mg (0.14 mmol) of ({17-[5-(trifluoromethyl)pyridin-3-yl]estra-1,3,5(10),16-tetraen-3-yl}oxy)acetic acid in 3 ml of 2-methyltetrahydrofuran, and the mixture was stirred at room temperature overnight. 0.5 ml of DMF was added, and the mixture was heated at 50° C. for 6 h. 0.34 ml of a 2M ethylamine solution in THF and 57 microliter of triethylamin were added, and the mixture was stirred at room temperature for 3 days. The reaction mixture was diluted with water and extracted three times with ethyl acetate, the combined organic phases were concentrated and the residue was purified by preparative HPLC. This gave 41 mg of the title compound. $C_{28}H_{31}F_3N_2O_2$. MS (ESIpos) mass found: 484.23. $^1$H-NMR (300 MHz, DMSO-d$_6$): δ [ppm]=0.93-1.07 (m, 6H), 1.33-1.66 (m, 4H), 1.73 (td, 1H), 1.83-1.92 (m, 1H), 2.05-2.41 (m, 5H), 2.76-2.86 (m, 2H), 3.06-3.16 (m, 2H), 4.34 (s, 2H), 6.32-6.38 (m, 1H), 6.62-6.72 (m, 2H), 7.15 (d, 1H), 7.97-8.06 (m, 2H), 8.81-8.85 (m, 1H), 8.88-8.92 (m, 1H).

Pharmacological Examination of the Compounds According to the Invention In Vitro Example 20

AKR1C3-Inhibitory Activity

The AKR1C3-inhibitory activity of the substances of the present invention was measured in the AKR1C3 assay described in the paragraphs below.

Essentially, the enzyme activity is measured by quantification of the Coumberol from Coumberone (Halim, M., Yee, D. J., and Sames, D., J. AM. CHEM. SOC. 130, 14123-14128 (2008) and Yee, D. J., Balsanek, V., Bauman, D. R., Penning, T. M., and Sames, D., Proc. Natl. Acad. Sci. USA 103, 13304-13309 (2006)). In this test, the increase of the highly fluorescent Coumberol by NADPH- (nicotinamide adenine dinucleotide phosphate)-dependent reduction of the non-fluorescent Coumberone by AKR1C3 can be determined.

The enzyme used was recombinant human AKR1C3 (Aldo-keto reductase family 1 member C3) (GenBank Accession No. NM_003739). This was expressed in E. coli as GST (glutathione S transferase) fusion protein and purified by glutathione Sepharose affinity chromatography. The GST was removed by digestion with thrombin and subsequent size exclusion chromatography (Dufort, I., Rheault, P., Huang, X F., Soucy, P., and Luu-The, V., Endocrinology 140, 568-574 (1999)).

For the assay, 50 nl of a 100-fold concentrated solution of the test substance in DMSO were pipetted into a black low-volume 384-well microtiter plate (Greiner Bio-One, Frickenhausen, Germany), 2.0 µl of a solution of AKR1C3 in assay buffer [50 mM potassium phosphate buffer pH 7, 1 mM DTT, 0.0022% (w/v) Pluronic F-127, 0.01% BSA (w/v) and protease inhibitor cocktail (Complete, EDTA-free Protease Inhibitor Cocktail from Roche)] were added and the mixture was incubated for 15 min to allow pre-binding of the substances to the enzyme prior to the enzyme reaction. The enzyme reaction was then started by addition of 3 µl of a solution of NADPH (16.7 µM→final concentration in 5 µl of assay volume is 10 µM) and Coumberone (0.5 µM→final concentration in 5 µl of assay volume is 0.3 µM) in assay buffer, and the resulting mixture was incubated at 22° C. for the reaction time of 90 min. The concentration of the AKR1C3 was adapted to the respective activity of the enzyme preparation and adjusted such that the assay was carried out in the linear range. Typical concentrations were in the region of 1 nM. The reaction was stopped by addition of 5 µl of a stop solution consisting of the inhibitor EM-1404 [F. Labrie et al. U.S. Pat. No. 6,541,463, 2003] (2 µM→final concentration in 5 µl of assay volume is 1 µM). The fluorescence of the Coumberole was then measured at 520 nm (excitation at 380 nm) using a suitable measuring instrument (Pherastar from BMG Labtechnologies). The intensity of the fluorescence was used as a measure of the amount of Coumberole formed and thus of the enzyme activity of AKR1C3. The data were normalized (enzyme reaction without inhibitor=0% inhibition; all other assay components, but no enzyme=100% inhibition). Usually, the test substances were tested on the same microtiter plate at 11 different concentrations in the range from 20 µM to 96.8 pM (20 µM, 5.9 µM, 1.7 µM, 0.5 µM, 0.15 µM, 44 nM, 12.9 nM, 3.8 nM, 1.1 nM, 0.3 nM and 96.8 pM, the dilution series were prepared prior to the assay on the level of the 100-fold concentrated solution by serial 1:3 dilutions with 100% DMSO) in double for each concentration, and the $IC_{50}$ values were calculated using a 4-parameter fit.

As described, the pharmacological substances claimed were examined for their inhibitory activity on the AKR1C3 enzyme (see Table 1). The compounds claimed show a strong inhibition of AKR1C3 in vitro ($IC_{50}$ values <200 nM) and in most cases even $IC_{50}$ values <50 nM.

TABLE 1

Inhibition of AKR1C3 of the compounds according to the invention (for some of the compounds, the values of two experimental determinations are stated)

| Example compound | AKR1C3 enzyme inhibition $IC_{50}$ [nmol/l] |
|---|---|
| 1 | 7.6 |
| 1 | 8.0 |
| 2 | 33 |
| 2 | 23 |
| 3 | 16 |
| 3 | 8.6 |
| 4 | 136 |
| 5 | 89 |
| 6 | 9.2 |
| 7 | 1.4 |
| 8 | 12 |

TABLE 1-continued

Inhibition of AKR1C3 of the compounds according to the invention (for some of the compounds, the values of two experimental determinations are stated)

| Example compound | AKR1C3 enzyme inhibition $IC_{50}$ [nmol/l] |
|---|---|
| 8 | 11 |
| 9 | 42 |
| 10 | 2.7 |
| 11 | 2.5 |
| 12 | 4.0 |
| 13 | 2.8 |
| 14 | 20 |
| 15 | 54 |
| 16 | 124 |
| 17 | 25 |
| 18 | 10 |
| 19 | 53 |

Example 21

Test for AKR1C3 Inhibition in a Cell-Based System

The inhibition of AKR1C3 by the substances described in the present invention was measured in a cell-based assay using coumberol as substrate for the AKR1C3 (Halim, M., Yee, D. J., and Sames, D., J. AM. CHEM. SOC. 130, 14123-14128 (2008) and Yee, D. J., Balsanek, V., Bauman, D. R., Penning, T. M., and Sames, D., Proc. Natl. Acad. Sci. USA 103, 13304-13309 (2006)) (cf. Example 20).

The cell system used were HEK293 cells (ATCC, USA) (cell culture medium: DMEM, 1.5 g glucose, 10% FCS, PSG). The cells were transfected in an AKR1C3 expression plasmid (pCMV6-AC-AKR1C3, GenBank Accession No. NM_003739.4) overnight (X-tremeGENE HP, Roche). The next morning, the cells were sown in black 96well cell culture plates at a cell density of 40000 cells/well (Greiner Bio-One, Frickenhausen, Germany). After 7 h, the cells were incubated with the test substances (dissolved in 100× concentration in DMSO, final concentration between $10^{-11}$M and $10^{-5}$M) and coumberol (dissolved in cell culture medium, final concentration $5\times10^{-6}$M) overnight. The next morning, the fluorescence of coumberol was measured at 535 nm (excitation at 355 nm) using a suitable measuring instrument (Mithras, from Berthold). The fluorescence intensity was used as a measure of the amount of coumberol formed and thus of the enzyme activity of AKR1C3. The data were normalized (transfected cells without inhibitor, only DMSO=0% inhibition; transfected cells, 10 µM inhibitor EM-1404 [F. Labrie et al. U.S. Pat. No. 6,541,463, 2003]=100% inhibition), and the $IC_{50}$ values were calculated using a 4-parameter fit.

In the cell-based assay described above, the pharmacological substances claimed were examined for their inhibitory activity on the AKR1C3 enzyme (see Table 2). The compounds showed a strong inhibition of cellular AKR1C3 in vitro ($IC_{50}$ values <300 nM) and in most cases even $IC_{50}$ values <100 nM.

TABLE 2

Inhibition of AKR1C3 of the compounds according to the invention (for some of the compounds, the values of independent experimental determinations are stated)

| Example compound | Cellular AKR1C3 inhibition IC50 [nmol/l] |
|---|---|
| 1 | 40 |
| 1 | 52 |
| 1 | 157 |
| 2 | 48 |
| 2 | 68 |
| 3 | 49 |
| 3 | 56 |
| 3 | 31 |
| 8 | 170 |
| 8 | 220 |

Example 22

AKR1C3 Binding

Binding of Example compound 1 to the AKR1C3 enzyme was measured by isothermal titration calorimetry. The degree of affinity of a given compound can be stated using the dissociation constant ($K_D$ value). Human AKR1C3 enzyme was prepared as described in Example 20. For ITC experiments, human AKR1C3 protein was transferred by gel permeation into a PBS buffer consisting of 137 mM NaCl, 2.7 mM KCl, 10 mM $Na_2HPO_4$, 2 mM $KH_2PO_4$ and 1 mM tris(2-carboxyethyl)phosphine hydrochloride. The compounds were dissolved in 100% DMSO at a concentration of 10 mM and then diluted with PBS buffer. Isothermal titration calorimetry experiments (ITC experiments) were carried out using an ITC200 titration calorimeter (GE Healthcare, Northampton, Mass., USA) at a temperature of 25° C. The change in enthalpy resulting from the injection of the protein was determined by integration of the calorimetric signal. The data were analyzed with Origin 7.0 (GE Healthcare, Northampton, Mass., USA). Heat of dilution values were determined using the last injection of the titration in question and subtracted prior to curve fitting. The protein concentration in the injection syringe was in the range from 80 to 120 μM, and the concentration of the compound to be measured was in the range from 5 to 20 μM.

A $K_D$ value of 230 nanomolar and an exothermal binding enthalpy of −1500 kcal/mol were determined for Example compound 1.

The invention claimed is:

1. A compound of the formula (I)

(I)

in which

A represents pyridin-3-yl, pyrimidin-5-yl, pyrimidin-4-yl, pyrazin-2-yl, pyridazin-4-yl, pyridazin-3-yl, optionally mono- or disubstituted by fluorine, chlorine, nitrile, hydroxyl, carboxyl, trifluoromethyl, pentafluoroethyl, methoxy, ethoxy, trifluoromethoxy, —$OCH_2CF_3$, —$SO_2CH_3$, —$SO_2CH_2CH_3$, —(C=O)$CH_3$, $C_1$-$C_4$-Alkyl, —$CH_2OH$, —$C(CH_3)_2OH$, —$CONH_2$, —(C=O)$NHCH_3$, —(C=O)$NHCH_2CH_3$, —(C=O)N($CH_3$)$_2$, —$SO_2NH_2$, —$SO_2NHCH_3$, —$SO_2N(CH_3)_2$, $R^1$ represents —O—$CR^aR^b$—Y where $R^a$ and $R^b$ independently of one another represent represent hydrogen, methyl, ethyl, propyl, isopropyl, phenyl, 4-fluorophenyl, 3-fluorophenyl, 2-fluorophenyl, $CH_3$—O—$CH_2$—, —$CH_2CF_3$ or $R^a$ and $R^b$ together represent —($CH_2$)$_n$— where n=2, 3, 4 or 5 or $R^a$ and $R^b$ together represent —$CH_2$—O—$CH_2$—, —$CH_2$—NH—$CH_2$—, —$CH_2$—N($CH_3$)—$CH_2$—, —$CH_2CH_2$—O—$CH_2CH_2$—, —$CH_2CH_2$—NH—$CH_2CH_2$—, —$CH_2CH_2$—N($CH_3$)—$CH_2CH_2$—

—O—$CR^cR^d$—$CR^eR^f$—Y where $R^c$, $R^d$, $R^eR^f$ represent hydrogen or $R^e$, $R^f$ represent hydrogen and $R^c$, $R^d$ independently of one another represent methyl, ethyl or together represent —($CH_2$)$_n$— where n=2, 3, 4, 5 or together represent —$CH_2$—O—$CH_2$— or —$CH_2CH_2$—O—$CH_2CH_2$— or $R^c$, $R^d$ represent hydrogen and $R^e$, $R^f$ independently of one another represent methyl, ethyl, $CF_3CH_2$— or together represent —($CH_2$)n- where n=2, 3, 4, 5, —$CH_2CH_2$—O—$CH_2CH_2$—, —$CH_2CH_2$—NH—$CH_2CH_2$—, —$CH_2CH_2$—N($CH_3$)—$CH_2CH_2$—, —$CH_2$—O—$CH_2$—, —$CH_2$—NH—$CH_2$—, —$CH_2$—N($CH_3$)—$CH_2$— or $R^d$, $R^e$, $R^f$ represent hydrogen and $R^e$ represents methyl, ethyl, trifluoromethyl or $R^c$, $R^d$, $R^f$ represent hydrogen and $R^e$ represents methyl, ethyl, trifluoromethyl, hydroxyl, methoxy, trifluoromethoxy or $R^d$, $R^f$ represent hydrogen and $R^c$, $R^e$ independently of one another represent methyl, ethyl, trifluoromethyl,

—O—$CH_2CH_2CH_2$—Y,

—O—$CH_2C(CH_3)_2CH_2$—Y,

—O—$CH_2CH_2C(CH_3)_2$—Y,

—O—$CH_2CH_2CH(CH_3)$—Y,

—O—$CH_2$—CH(OH)—$CH_2$—Y

—O$CH_2CH_2CH_2CH_2$—Y,

—$CH_2$—Y,

—$CR^gR^h$—$CR^iR^j$—Y where $R^g$, $R^h$, $R^i$, $R^j$ represent hydrogen or $R^g$, $R^h$, $R^i$ represent hydrogen and $R^j$ represents methyl, ethyl, trifluoromethyl or $R^i$, $R^j$ represent hydrogen and $R^g$, $R^h$ represent methyl or together represent —$CH_2$—, —$CH_2CH_2$—, —$CH_2CH_2CH_2$— or $R^g$ represents methyl and $R^h$, $R^i$, $R^j$ represent hydrogen,

—$CH_2CH_2CH_2$—Y,

—$CH_2CH_2C(CH_3)_2$—Y or

—$CH_2CH_2CH_2CH_2$—Y and

Y represents —$CO_2H$, —OH, —(C=O)$NH_2$, —(C=O)NH$C_{1-4}$-alkyl, —S(=O)$CH_3$ or a salt thereof.

2. The compounds of claim 1, in which

A represents pyridin-3-yl, pyrimidin-5-yl, pyrimidin-4-yl, pyrazin-2-yl, pyridazin-4-yl, pyridazin-3-yl, optionally monosubstituted by fluorine, chlorine, nitrile, hydroxyl, carboxyl, trifluoromethyl, methoxy, ethoxy, trifluoromethoxy, —$SO_2CH_3$, —(C=O)$CH_3$, $C_1$-$C_4$-alkyl, R¹ represents —O—CR$^a$R$^b$—Y where
R$^a$ and R$^b$ independently of one another represent represent hydrogen, methyl, ethyl, propyl, isopropyl, phenyl, $CH_3$—O—$CH_2$—, $CF_3CH_2$—,
—O—CR$^c$R$^d$—CR$^e$R$^f$—Y where
R$^c$, R$^d$, R$^e$R$^f$ represent hydrogen or
R$^c$, R$^d$ represent hydrogen and R$^e$, R$^f$ independently of one another represent methyl, ethyl, $CF_3CH_2$— or
R$^d$, R$^e$, R$^f$ represent hydrogen and R$^c$ represents methyl, ethyl or
R$^c$, R$^d$, R$^f$ represent hydrogen and R$^e$ represents methyl, ethyl,
—O—$CH_2CH_2CH_2$—Y,
—O—$CH_2C(CH_3)_2CH_2$—Y,
—O—$CH_2CH_2C(CH_3)_2$—Y,
—O—$CH_2CH_2CH(CH_3)$—Y,
—O—$CH_2$—CH(OH)—$CH_2$—Y or
—CR$^g$R$^h$—CR$^i$R$^j$—Y where
R$^g$, R$^h$, R$^i$, R$^j$ represent hydrogen or
R$^g$, R$^h$, R$^i$ represent hydrogen and R$^j$ represents methyl, ethyl or
R$^i$, R$^j$ represent hydrogen and R$^g$, R$^h$ represents methyl or
R$^g$ represents methyl and R$^h$, R$^i$, R$^j$ represent hydrogen
and
Y represents —$CO_2H$, —OH, —(C=O)$NH_2$, —(C=O)$NHC_{1-4}$-alkyl
or a salt thereof.

3. The compound of claim 1, in which
A represents pyridin-3-yl, pyrimidin-5-yl, pyridazin-4-yl, optionally monosubstituted by fluorine, carboxyl, trifluoromethyl, methyl
R¹ represents —O—CR$^a$R$^b$—Y where
R$^a$ and R$^b$ represent hydrogen or R$^a$ represents hydrogen and R$^b$ represents methyl, ethyl, phenyl or $CH_3$—O—$CH_2$—
—O—CR$^c$R$^d$—CR$^e$R$^f$—Y where
R$^c$, R$^d$ represent hydrogen and R$^e$, R$^f$ represent methyl
—O—$CH_2CH_2CH_2$—Y,
—O—$CH_2C(CH_3)_2CH_2$—Y,
—O—$CH_2$—CH(OH)—$CH_2$—Y or
—$CH_2$—$CH_2$—Y and
Y represents —$CO_2H$, —OH, —(C=O)$NH_2$, —(C=O)$NHC_{1-4}$-alkyl
or a salt thereof.

4. The compounds of formula (I) of claim 1 in which
A represents 5-fluoropyridin-3-yl, 5-(trifluoromethyl)pyridin-3-yl, 5-carboxypyridin-3-yl, 6-methylpyridin-3-yl, pyrimidin-5-yl, 6-methylpyridazin-4-yl and
R¹ represents —O—CR$^a$R$^b$—$CO_2H$,
—O—CR$^a$R$^b$—(C=O)$NH_2$,
—O—CR$^a$R$^b$—(C=O)$NHCH_2CH_3$ where
R$^a$ and R$^b$ represent hydrogen or
R$^a$ represents hydrogen and R$^b$ represents methyl, ethyl, phenyl, $CH_3OCH_2$—, —O—CR$^c$R$^d$—CR$^e$R$^f$—$CO_2H$ where
R$^c$, R$^d$ represent hydrogen and R$^e$, R$^f$ represent methyl,
—O—$CH_2CH_2CH_2$—OH,
—O—$CH_2CH_2CH_2$—$CO_2H$,
—O—$CH_2C(CH_3)_2CH_2$—OH or
—O—$CH_2$—CH(OH)—$CH_2$—OH
or a salt thereof.

5. The compound of claim 1, wherein the compound is selected from the group consisting of
3-[17-(5-fluoropyridin-3-yl)estra-1,3,5(10),16-tetraen-3-yl]propanoic acid,
({17-[5-(trifluoromethyl)pyridin-3-yl]estra-1,3,5(10),16-tetraen-3-yl}oxy)acetic acid,
{[17-(5-fluoropyridin-3-yl)estra-1,3,5(10),16-tetraen-3-yl]oxy}acetic acid,
{[17-(6-methylpyridin-3-yl)estra-1,3,5(10),16-tetraen-3-yl]oxy}acetic acid,
{[17-(pyrimidin-5-yl)estra-1,3,5(10),16-tetraen-3-yl]oxy}acetic acid,
5-[3-(carboxymethoxy)estra-1,3,5(10),16-tetraen-17-yl]nicotinic acid,
{[17-(6-methylpyridazin-4-yl)estra-1,3,5(10),16-tetraen-3-yl]oxy}acetic acid,
3-{[17-(5-fluoropyridin-3-yl)estra-1,3,5(10),16-tetraen-3-yl]oxy}-2,2-dimethylpropanoic acid,
4-{[17-(5-fluoropyridin-3-yl)estra-1,3,5(10),16-tetraen-3-yl]oxy}butanoic acid,
2-{[17-(5-fluoropyridin-3-yl)estra-1,3,5(10),16-tetraen-3-yl]oxy}propanoic acid,
2-{[17-(5-fluoropyridin-3-yl)estra-1,3,5(10),16-tetraen-3-yl]oxy}butanoic acid,
2-{[17-(5-fluoropyridin-3-yl)estra-1,3,5(10),16-tetraen-3-yl]oxy}-3-methoxypropanoic acid,
2-{[17-(3-pyridyl)estra-1,3,5(10),16-tetraen-3-yl]oxy}propanoic acid,
2-{[17-(5-fluoropyridin-3-yl)estra-1,3,5(10),16-tetraen-3-yl]oxy}propanamide,
3-{[17-(5-fluoropyridin-3-yl)estra-1,3,5(10),16-tetraen-3-yl]oxy}propan-1-ol,
3-{[17-(5-fluoropyridin-3-yl)estra-1,3,5(10),16-tetraen-3-yl]oxy}-2,2-dimethylpropan-1-ol,
3-{[17-(5-fluoropyridin-3-yl)estra-1,3,5(10),16-tetraen-3-yl]oxy}propan-1,2-diol, {[17-(5-fluoropyridin-3-yl)estra-1,3,5(10),16-tetraen-3-yl]oxy}(phenyl)acetic acid,
N-ethyl-2-({17-[5-(trifluoromethyl)pyridin-3-yl]estra-1,3,5(10),16-tetraen-3-yl}oxy)acetamide,
or a salt thereof.

6. A method of treatment of endometriosis, of uterine leiomyomas, of uterine bleeding disorders, of dysmenorrhoea, of prostate carcinoma, of prostate hyperplasia, of acne, of seborrhoea, of hair loss, of premature sexual maturity, of polycystic ovary syndrome, of breast cancer, of lung cancer, of endometrial carcinoma, of renal cell carcinoma, of bladder carcinoma, of non-Hodgkin lymphomas, of chronic obstructive pulmonary disease (COPD), of adiposity or of inflammatory pain comprising administering an effective amount of a compound of claim 1 to a human or animal in need thereof.

7. A medicament comprising a compound of claim 1 and at least one further active compound.

8. A medicament comprising a compound of claim 1 and an inert non-toxic pharmaceutically suitable auxiliary.

9. A method of treatment of endometriosis, of uterine leiomyomas, of uterine bleeding disorders, of dysmenorrhoea, of prostate carcinoma, of prostate hyperplasia, of acne, of seborrhoea, of hair loss, of premature sexual maturity, of polycystic ovary syndrome, of breast cancer, of lung cancer, of endometrial carcinoma, of renal cell carcinoma, of bladder carcinoma, of non-Hodgkin lymphomas, of chronic obstructive pulmonary disease (COPD), of adiposity or of inflammatory pain comprising administering an effective amount of a medicament of claim 8 to a human or animal in need thereof.

10. A method of treatment of endometriosis in humans and animals by administration of 0.01 to 1000 mg/kg body weight per day of at least one compound of claim 1 to a human or animal in need thereof.

* * * * *